(12) United States Patent
Mears et al.

(10) Patent No.: US 12,300,381 B2
(45) Date of Patent: *May 13, 2025

(54) SCORING, EVALUATION, AND FEEDBACK RELATED TO EMS CLINICAL AND OPERATIONAL PERFORMANCE

(71) Applicant: ZOLL Medical Corporation, Chelmsford, MA (US)

(72) Inventors: Gregory D. Mears, Carolina Beach, NC (US); Gary A. Freeman, Waltham, MA (US); Matthew F. Pesce, Littleton, CO (US)

(73) Assignee: ZOLL Medical Corporation, Chelmsford, MA (US)

( * ) Notice: Subject to any disclaimer, the term of this patent is extended or adjusted under 35 U.S.C. 154(b) by 168 days.

This patent is subject to a terminal disclaimer.

(21) Appl. No.: 17/738,840

(22) Filed: May 6, 2022

(65) Prior Publication Data

US 2022/0262502 A1 Aug. 18, 2022

Related U.S. Application Data

(63) Continuation of application No. 16/289,498, filed on Feb. 28, 2019, now Pat. No. 11,355,233, which is a
(Continued)

(51) Int. Cl.
*G16H 40/20* (2018.01)
*G16H 50/20* (2018.01)
(Continued)

(52) U.S. Cl.
CPC ............. *G16H 40/20* (2018.01); *G16H 50/20* (2018.01); *G16H 50/70* (2018.01); *G16H 10/60* (2018.01)

(58) Field of Classification Search
CPC ........ G16H 40/20; G16H 50/20; G16H 50/70; G16H 10/60
See application file for complete search history.

(56) References Cited

U.S. PATENT DOCUMENTS

| 4,945,759 A | 8/1990 | Krofchalk et al. |
| 5,085,224 A | 2/1992 | Galen et al. |

(Continued)

FOREIGN PATENT DOCUMENTS

| EP | 1538025 A1 | 6/2005 |
| WO | 19920021116 A1 | 11/1992 |

(Continued)

OTHER PUBLICATIONS

Chu, Yuechun et al., "A Mobile Teletrauma System Using 3G Networks," IEEE Transactions on Information Technology in Biomedicine, vol. 8, No. 4, pp. 456-462 Dec. 2004.
(Continued)

*Primary Examiner* — Maroun P Kanaan
(74) *Attorney, Agent, or Firm* — Finch & Maloney PLLC

(57) ABSTRACT

A method for evaluating emergency medical service according to embodiments of the present invention includes receiving emergency medical service data from a database, filtering the emergency medical service data based on a selection criteria to form a filtered emergency medical service data set, determining a first score from the filtered emergency medical service data set, where the first score indicates objective clinical performance quality for the filtered emergency medical service data set, determining a second score from the filtered emergency medical service data set, where the second score indicates objective operational performance quality for the filtered emergency medical service
(Continued)

data set, merging the first score and the second score to form a composite score; and visually displaying the composite score to a user.

22 Claims, 13 Drawing Sheets

Related U.S. Application Data continuation of application No. 14/270,477, filed on May 6, 2014, now Pat. No. 10,262,758.

(60) Provisional application No. 61/822,080, filed on May 10, 2013.

(51) Int. Cl.
*G16H 50/70* (2018.01)
*G16H 10/60* (2018.01)

(56) References Cited

U.S. PATENT DOCUMENTS

| | | |
|---|---|---|
| 5,208,754 A | 5/1993 | Nakaura et al. |
| 5,224,485 A | 7/1993 | Powers et al. |
| 5,319,363 A | 6/1994 | Welch et al. |
| 5,333,617 A | 8/1994 | Hafner |
| 5,343,869 A | 9/1994 | Pross et al. |
| 5,483,452 A | 1/1996 | Tanaka |
| 5,494,051 A | 2/1996 | Schneider, Sr. |
| 5,511,553 A | 4/1996 | Seqalowitz |
| 5,531,472 A | 7/1996 | Semchena et al. |
| 5,544,661 A | 8/1996 | Davis et al. |
| 5,549,659 A | 8/1996 | Johansen et al. |
| 5,570,127 A | 10/1996 | Schmidt |
| 5,574,443 A | 11/1996 | Hsieh |
| 5,593,426 A | 1/1997 | Morgan et al. |
| 5,646,994 A | 7/1997 | Hill |
| 5,680,123 A | 10/1997 | Lee |
| 5,782,878 A | 7/1998 | Morgan et al. |
| 5,793,420 A | 8/1998 | Schmidt |
| 5,959,529 A | 9/1999 | Kail, IV |
| 5,978,017 A | 11/1999 | Tino |
| 6,002,326 A | 12/1999 | Turner |
| 6,117,073 A | 9/2000 | Jones et al. |
| 6,141,584 A | 10/2000 | Rockwell et al. |
| 6,188,939 B1 | 2/2001 | Morgan et al. |
| 6,211,907 B1 | 4/2001 | Scaman et al. |
| 6,321,113 B1 | 11/2001 | Parker et al. |
| 6,389,339 B1 | 5/2002 | Just |
| 6,389,340 B1 | 5/2002 | Rayner |
| 6,390,996 B1 | 5/2002 | Halperin et al. |
| 6,398,744 B2 | 6/2002 | Bystrom et al. |
| 6,405,083 B1 | 6/2002 | Rockwell et al. |
| 6,481,887 B1 | 11/2002 | Mirabella |
| 6,526,219 B1 | 2/2003 | Posa et al. |
| 6,532,381 B2 | 3/2003 | Bayer et al. |
| 6,593,848 B1 | 7/2003 | Atkins, III |
| 6,604,115 B1 | 8/2003 | Garv, Jr. et al. |
| 6,681,003 B2 | 1/2004 | Linder et al. |
| 6,727,814 B2 | 4/2004 | Saltzstein et al. |
| 6,747,556 B2 | 6/2004 | Medema et al. |
| 6,827,695 B2 | 12/2004 | Palazzolo et al. |
| 6,829,501 B2 | 12/2004 | Nielsen et al. |
| 6,831,556 B1 | 12/2004 | Boykin |
| 6,927,674 B2 | 8/2005 | Harter, Jr. et al. |
| 6,937,150 B2 | 8/2005 | Medema et al. |
| 6,950,013 B2 | 9/2005 | Scaman et al. |
| 6,957,102 B2 | 10/2005 | Silver et al. |
| 6,993,386 B2 | 1/2006 | Lin et al. |
| 7,006,865 B1 | 2/2006 | Cohen et al. |
| 7,092,802 B2 | 8/2006 | Baldassa |
| 7,118,542 B2 | 10/2006 | Palazzolo et al. |
| 7,120,488 B2 | 10/2006 | Nova et al. |
| 7,122,014 B2 | 10/2006 | Palazzolo et al. |
| 7,129,836 B2 | 10/2006 | Lawson et al. |
| 7,162,306 B2 | 1/2007 | Caby et al. |
| 7,172,300 B2 | 2/2007 | Plaster |
| 7,202,792 B2 | 4/2007 | Zhang et al. |
| 7,231,258 B2 | 6/2007 | Moore et al. |
| 7,233,905 B1 | 6/2007 | Hutton et al. |
| 7,295,871 B2 | 11/2007 | Halperin et al. |
| 7,349,777 B2 | 3/2008 | Silverbrook |
| 7,356,392 B2 | 4/2008 | Hubbard et al. |
| 7,380,951 B2 | 6/2008 | Plaster |
| 7,382,771 B2 | 6/2008 | Leblanc et al. |
| 7,386,376 B2 | 6/2008 | Basir et al. |
| 7,395,096 B2 | 7/2008 | Baratono et al. |
| 7,412,395 B2 | 8/2008 | Rowlandson |
| 7,425,889 B2 | 9/2008 | Widmann et al. |
| 7,436,429 B2 | 10/2008 | Tillotson |
| 7,444,315 B2 | 10/2008 | Wu |
| 7,496,439 B2 | 2/2009 | McCormick |
| 7,548,803 B2 | 6/2009 | Maccarthy |
| 7,564,479 B2 | 7/2009 | Schedivy |
| 7,650,291 B2 | 1/2010 | Rosenfeld et al. |
| 7,659,827 B2 | 2/2010 | Gunderson et al. |
| 7,768,548 B2 | 8/2010 | Silvernail et al. |
| 7,804,426 B2 | 9/2010 | Etcheson |
| 7,830,962 B1 | 11/2010 | Fernandez et al. |
| 7,840,277 B2 | 11/2010 | Matos |
| 7,912,646 B2 | 3/2011 | McCarthy et al. |
| 7,983,811 B2 | 7/2011 | Basir et al. |
| 8,010,286 B2 | 8/2011 | Templeton et al. |
| 8,045,685 B2 | 10/2011 | Lin et al. |
| 8,054,168 B2 | 11/2011 | McCormick et al. |
| 8,126,309 B2 | 2/2012 | Sakai |
| 8,149,108 B2 | 4/2012 | Hamel et al. |
| 8,215,422 B2 | 7/2012 | Abel |
| 8,630,768 B2 | 1/2014 | McClellan et al. |
| 8,666,590 B2 | 3/2014 | Follmer et al. |
| 8,930,040 B2 | 1/2015 | Gompert et al. |
| 9,311,763 B2 | 4/2016 | Gompert et al. |
| 2001/0044732 A1 | 11/2001 | Maus et al. |
| 2002/0004729 A1 | 1/2002 | Zak et al. |
| 2002/0017405 A1 | 2/2002 | Nada |
| 2004/0077995 A1 | 4/2004 | Ferek-Petric et al. |
| 2005/0055245 A1* | 3/2005 | Oster ............... G16H 40/20 705/2 |
| 2005/0137929 A1 | 6/2005 | Frazier et al. |
| 2005/0277872 A1 | 12/2005 | Colby et al. |
| 2005/0283438 A1 | 12/2005 | Brownewell et al. |
| 2006/0009809 A1 | 1/2006 | Marcovecchio et al. |
| 2006/0149597 A1 | 7/2006 | Powell et al. |
| 2006/0287586 A1 | 12/2006 | Murphy |
| 2007/0100213 A1 | 5/2007 | Dossas et al. |
| 2007/0118038 A1 | 5/2007 | Bodecker et al. |
| 2007/0203742 A1 | 8/2007 | Jones et al. |
| 2007/0255120 A1 | 11/2007 | Rosnov |
| 2007/0276300 A1 | 11/2007 | Olson et al. |
| 2007/0299689 A1 | 12/2007 | Jones et al. |
| 2008/0018454 A1 | 1/2008 | Chan et al. |
| 2008/0042813 A1 | 2/2008 | Wheatley et al. |
| 2008/0126134 A1 | 5/2008 | Jones et al. |
| 2008/0225762 A1 | 9/2008 | Soliman |
| 2008/0252412 A1 | 10/2008 | Larsson et al. |
| 2008/0300731 A1 | 12/2008 | Nakajima et al. |
| 2008/0319604 A1 | 12/2008 | Follmer et al. |
| 2009/0063187 A1 | 3/2009 | Johnson et al. |
| 2009/0222539 A1 | 9/2009 | Lewis et al. |
| 2009/0312998 A1 | 12/2009 | Berckmans et al. |
| 2010/0088010 A1 | 4/2010 | Verdejo et al. |
| 2010/0185341 A1 | 7/2010 | Wilson et al. |
| 2010/0298899 A1 | 11/2010 | Donnelly et al. |
| 2011/0117878 A1 | 5/2011 | Barash et al. |
| 2011/0124974 A1 | 5/2011 | Martin et al. |
| 2011/0133951 A1 | 6/2011 | Palmieri |
| 2011/0153372 A1 | 6/2011 | Weinstock et al. |
| 2011/0184759 A1 | 7/2011 | Selker et al. |
| 2011/0263946 A1 | 10/2011 | el Kaliouby et al. |
| 2011/0295078 A1 | 12/2011 | Reid et al. |
| 2011/0295446 A1 | 12/2011 | Basir et al. |
| 2012/0004804 A1 | 1/2012 | Beams et al. |
| 2012/0035948 A1 | 2/2012 | Borton et al. |

(56) References Cited

U.S. PATENT DOCUMENTS

| | | | |
|---|---|---|---|
| 2012/0092497 | A1 | 4/2012 | Hoetzer et al. |
| 2012/0123224 | A1 | 5/2012 | Packer et al. |
| 2012/0191476 | A1* | 7/2012 | Reid .................. G16H 10/65 |
| | | | 705/3 |
| 2012/0295576 | A1 | 11/2012 | Peterson |
| 2012/0313792 | A1 | 12/2012 | Behm et al. |
| 2013/0096649 | A1 | 4/2013 | Martin et al. |
| 2013/0296719 | A1 | 11/2013 | Packer et al. |
| 2013/0304146 | A1 | 11/2013 | Aoyama et al. |
| 2014/0062118 | A1 | 3/2014 | Bourqraf et al. |
| 2014/0337047 | A1 | 11/2014 | Mears et al. |
| 2016/0180609 | A1 | 6/2016 | Gompert et al. |

FOREIGN PATENT DOCUMENTS

| | | |
|---|---|---|
| WO | 2006086089 A1 | 8/2006 |
| WO | 2011127459 A1 | 10/2011 |
| WO | 2012026922 A1 | 3/2012 |

OTHER PUBLICATIONS

Correspondence from Barry Chapin to Benjamin Fernandez dated Jan. 7, 2013 (2 pages).

Zoorob, Roger J. and James S. Campbell, M.D., "Acute Dyspnea in the Office," American Family Physician, Nov. 1, 2003, retrieved on Jan. 22, 2016 from nttp:i!www.aafp.org/afpi2003/1101/p1803 htm !?printable:::afp. (6 pages).

Gagliano, "Wireless Ambulance Telemedicine May Lessen Stroke Morbidity," Telemedicine Today, [online] [retrieved on Aug. 30, 2013] retrieved from nttpirwww2.telemedtoday.comia:ticles/wirelessamnulance.shtml. (2 pages).

Google search for the term "transmission of electrocardiograms from a moving ambulance", [retrieved on Sep. 10, 2013] retrieved from https://www.google.com/search?q=transmission+of+electrocardiograms+from+a-+moving+ambulance&oq=transmission+of+electrocardiograms+fro&aqs=chrome.1.6-9i57j0.12049j0&sourceid=chrome&ie=UTF-8. (85 pages).

Imielinski, et al. (Eds), Mobile Computing, Kluwer Academic Publishers, 2000, 1996 [online] [retrived on Sep. 12, 3013] retrieved from Google Books at http://books.google.com/books?id=gx3HVwcEOZAC&pg=PA624&dq=portab- le+medical+locating+a+portable+wireless+communication+network&hl=en&sa=X&e-i=5XfAUaXqGsbn0QGMIoHoCw&ved=0CBsQ6AEwAQ#v=onepage&q=portable%20medical%20- locating%20a%20portable%20wireless%20communication%20network&f=false.(1 page).

ZOLL Data Systems, Workflow Editor User's Guide, Software version 5.00 Manual 1.00 revision 0, 40 pages, 2007.

Jain et al., "Towards a Comprehensive Technology for Recording and Analysis of Mulitple Physiological Parameters within their Behavioral and Environmental Context," [online] [retrieved on Aug. 23, 2013]. Retrieved from http://www.psych-methoden.uni-koeln.de/mitarbeiter/jain/jain- 6.htm. (12 pages).

Johnson, et al., "Remote Physiological Monitoring in the Home," in: Medical Informatics Europe '96: Human Facets in Information Technology (IOS Press, 1996, pp. 63-66).

Konoske, et al., "Evaluation of the Mobile Medical Monitor (M3) at Forward Levels of Care," Naval Health Research Center, Technical Document No. 98-2B, dated Sep. 1998 (47 pages).

Lee, et al., "Informatics in Prehospital Care," Trauma Informatics Computers in Health Care 1998, pp. 31-44 (abstract) (1 page).

Nam, "Development of remote diagnosis system integrating digital telemetry for medicine," Engineering in Medicine and Biology Society, 1998. Proceedings of the 20th Annual International Conference of the IEEE (vol. 3) (abstract) (1 page).

Pahlavan, Kaveh et al., "An Overview of Wireless Indoor Geolocation Techniques and Systems," C.G. Omidyar (Ed.): MWCN 2000, LNCS 1818, pp. 1-13, Springer-Verlag Berlin Heidelberg 2000.

Poor, Robert, "Wireless Mesh Networks," Sensors, Feb. 1, 2003, retrieved on Aug. 2, 2012 from http://www.sensorsmag.com/networking-communications/standards-protocols/wireless-mesh- networks-968. (7 pages).

Schaldach, "Pacemaker Technology," Electrotherapy of the Heart, 1992, pp. 47-72 (abstract) (1 page).

ScienceDaily, "Telemedicine on Ambulances May Save Stroke Patients," Feb. 6, 1998 [online] [retrieved Aug. 23, 2013] [retrieved from http://www.sciencedaily.com/releases/1998/02!980206071314.htrn. (3 pages).

Weiss, "Implications of silicon monolithic RFICs for medical instrumentation and telemetry," Silicon Monolithic Integrated Circuits in RF Systems, 1998. Digest of Papers, Sep. 18, 1998 (abstract) (1 page).

ZOLL Data systems, ePCR Suite 5.0.2 Release Notes, 2 pages, Feb. 15, 2008.

ZOLL Data Systems, Hardware and Software Specifications, RescueNet Tablet PCR(TM), Tablet PCR Version 4.04, 22 pages, Nov. 2006.

ZOLL Data Systems, RescueNet TabletPCR 4.04 Install Guide, 30 pages, Nov. 15, 2006.

ZOLL Data Systems, RescueNet TabletPCR User's Guide, Software version 5.0 Manual 5.0 revision 1, 102 pages, 2007.

ZOLL Data Systems, RescueNet TabletPCR 4.04 Known Issues, 1 page, Dec. 5, 2006.

ZOLL Data Systems, RescueNet TabletPCR User's Guide, Software version 4.04 Manual 4.0 revision 4, 100 pages, 2006.

ZOLL Data Systems, TabletPCR Version 4.04 Upgrade Guide, 28 pages, Nov. 15, 2006.

ZOLL Data Systems, RescueNet ePCR Suite 4.04 to 5.0.2 Upgrade Guide, 83 pages, Apr. 14, 2008.

ZOLL Data Systems, RescueNet ePCR Suite 5.0 Hardware and Software Specifications Version 5.0, 33 paoes, Jan. 24, 2014.

ZOLL Data Systems, RescueNet ePCR Suite 5.0 Install Guide, 70 pages, Jun. 25, 2007.

ZOLL Data Systems, RescueNet ePCR Suite 5.0 Install Guide, Applies to new installs of RescueNet ePCR Suite Version 5.0.1.x, 84 pages, Nov. 28, 2007.

ZOLL Data Systems, RescueNet ePCR Suite 5.0.1 Upgrade Guide, 82 pages, Nov. 16, 2007.

ZOLL Data Systems, RescueNet ePCR Suite 5.0.2 Install Guide, 83 pages, Apr. 14, 2008.

ZOLL Data Systems, RescueNet ePCR Suite Security Overview, 4 pages, Feb. 5, 2008.

ZOLL Data Systems, RescueNet ePCR Suite Upgrade Guide, applies to upgrades of RescueNet ePCR Suite 5.0.1 to version 5.0.2, 28 pages, Apr. 14, 2008.

ZOLL Data Systems, RescueNet ePCR User and Administration Guide, Software version 5.00 Manual 1.00 revision 0, Chapters 1-34, 588 pages, 2007.

ZOLL Data Systems, RescueNet Field Data Administrator's Guide, Software version 4.04 Manual 4.0 revision 4, 282 pages, 2006.

Pavlopoulos, et al., "Ambulance—mobile unit for health care provision via telmatics support," Engineering in Medicine and Biology Society, 1996 Bridging Disciplines for Biomedicine. Proceedings of the 18th Annual International Conference of the IEEE (vol. 3) (abstract) (1 page).

* cited by examiner

E02_04: Type of Service Requested
E02_20: Response Mode to Scene
E05_02: PSAP Call Date/Time
E05_04: Unit Notified by Dispatch Date/Time
E05_05: Unit En Route Date/Time
E05_06: Unit Arrived on Scene Date/Time
E05_09: Unit Left Scene Date/Time
E05_10: Patient Arrived at Destination Date/Time
E06_11: Gender
E06_12: Race
E06_14: Age
E06_15: Age Units
E09_15: Providers Primary Impression
E14_01: Date/Time Vital Signs Taken
E14_03: Cardiac Rhythm
E14_04: Systolic Blood Pressure
E14_07: Pulse Rate
E14_11: Respiratory Rate
E17_01: Protocols Used
E18_03: Medication Given
E09_01: Prior Aid
E19_03: Procedure
E20_01: Destination Name
E20_10: Incident/Patient Disposition
E20_14: Transport Mode from Scene
E22_01: Emergency Department Disposition
E22_02: Hospital Disposition
Required Medications for each EMS Protocol in E17_01
Required Procedures for each EMS Protocol in E17_01
Additional Documentation of a STEMI Patient (if collected via a custom data element within a proprietary patient care record software)

FIG. 3

| Performance Measure | Points | Clinical | Operational |
|---|---|---|---|
| 1. Dispatch Center Time | 0.8 | | X |
| 2. Wheels Rolling Time | 0.9 | | X |
| 3. Scene Time < 15 Minutes | 0.6 | | X |
| 4. Time to 12 Lead ECG | 0.5 | X | |
| 5. Symptom Onset Documentation | 0.9 | X | |
| 6. VS Documentation | 0.9 | X | |
| 7. 12 Lead ECG Documentation | 0.8 | X | |
| 8. ASA Administration | 0.5 | X | |
| 9. PCI Destination | 0.4 | | X |
| 10. Protocol Compliance | 0.3 | X | |
| Total STEMI Score | 6.6 | | |

FIG. 14

SCORING, EVALUATION, AND FEEDBACK RELATED TO EMS CLINICAL AND OPERATIONAL PERFORMANCE

CROSS REFERENCE TO RELATED APPLICATIONS

This application claims the benefit under 35 U.S.C. § 120 as a continuation of U.S. application Ser. No. 16/289,498, titled "SCORING, EVALUATION, AND FEEDBACK RELATED TO EMS CLINICAL AND OPERATIONAL PERFORMANCE" filed Feb. 28, 2019, which claims the benefit under 35 U.S.C. § 120 as a continuation of U.S. application Ser. No. 14/270,477, titled "SCORING, EVALUATION, AND FEEDBACK RELATED TO EMS CLINICAL AND OPERATIONAL PERFORMANCE" filed May 6, 2014, which claims priority under 35 U.S.C. § 119(e) to U.S. Provisional Application Ser. No. 61/822,080, titled "SCORING, EVALUATION, AND FEEDBACK RELATED TO EMS CLINICAL AND OPERATIONAL PERFORMANCE" filed on May 10, 2013, each of which is hereby incorporated herein by reference in its entirety.

TECHNICAL FIELD

Embodiments of the present invention relate generally to systems and methods for emergency medical service evaluation and scoring.

BACKGROUND

A response by emergency medical personnel to a patient medical event involves various clinical and operational efforts. Existing systems for evaluating performance or effectiveness of the emergency response often focus on one limited aspect of the response or service, and often involve subjective assessments and inconsistencies of evaluation approach which do not permit an objective comparison of one emergency services/response system with another emergency services/response system. Existing ranking and/or accreditation systems also often fail to account for both clinical and operational performance.

SUMMARY

In Example 1, a method for evaluating emergency medical service according to embodiments of the present invention includes receiving emergency medical service data from a database; filtering the emergency medical service data based on a selection criteria to form a filtered emergency medical service data set; determining a first score from the filtered emergency medical service data set, wherein the first score indicates objective clinical performance quality for the filtered emergency medical service data set; determining a second score from the filtered emergency medical service data set, wherein the second score indicates objective operational performance quality for the filtered emergency medical service data set; merging the first score and the second score to form a composite score; and visually displaying the composite score to a user.

In Example 2, the method of Example 1, further comprising displaying a recommendation to the user for improving the composite score.

In Example 3, the method of any of Examples 1-2, wherein the emergency medical service data in the database is at least partly in National EMS Information System (NEMSIS) format.

In Example 4, the method of any of Examples 1-3, wherein the selection criteria is patient age.

In Example 5, the method of any of Examples 1-4, wherein the selection criteria is patients having ST elevated myocardial infarction (STEMI).

In Example 6, the method of any of Examples 1-5, wherein the first score is selected from a group consisting of: a first clinical score indicating how rapidly a twelve lead ECG signal is acquired from a patient after arrival of an emergency medical team at a location of a medical emergency; a second clinical score indicating a proportion of patients whose symptom onset information is documented; a third clinical score indicating a proportion of patients whose vital signs are documented; a fourth clinical score indicating a proportion of patients whose twelve lead ECG signal is documented; a fifth clinical score indicating a proportion of patients who need aspirin and who are actually administered aspirin; and a sixth clinical score indicating a proportion of patients for which a treatment or diagnosis protocol applies and for which such treatment or diagnosis protocol is actually followed.

In Example 7, the method of any of Examples 1-6, further comprising: determining a third score from the filtered emergency medical service data set, wherein the third score indicates objective clinical performance quality for the filtered emergency medical service data set, wherein the first score and third score are each a different clinical score selected from the group consisting of the first, second, third, fourth, fifth, and sixth clinical scores, and merging the first, second, and third scores to form the composite score.

In Example 8, the method of any of Examples 1-7, further comprising: determining a fourth score from the filtered emergency medical service data set, wherein the fourth score indicates objective clinical performance quality for the filtered emergency medical service data set, wherein the first, third, and fourth scores are each a different clinical score selected from the group consisting of the first, second, third, fourth, fifth, and sixth clinical scores, and merging the first, second, third, and fourth scores to form the composite score.

In Example 9, the method of any of Examples 1-8, further comprising: determining a fifth, sixth, and seventh score from the filtered emergency medical service data set, wherein the fifth, sixth, and seventh scores each indicate objective clinical performance quality for the filtered emergency medical service data set, wherein the first, third, fourth, fifth, sixth, and seventh scores are each a different clinical score selected from the group consisting of the first, second, third, fourth, fifth, and sixth clinical scores, and merging the first, second, third, fourth, fifth, sixth, and seventh scores to form the composite score.

In Example 10, the method of any of Examples 1-9, wherein the second score is selected from a group consisting of: a first operational score indicating how rapidly a dispatch center receives an emergency communication and notifies an emergency medical team; a second operational score indicating how rapidly the emergency medical team receives notification from the dispatch center and begins traveling to a location of a medical emergency; a third operational score indicating a duration for which the emergency medical team remains at the location of the medical emergency; and a fourth operational score indicating a proportion of patients who need percutaneous coronary intervention (PCI) and are transported to a medical facility with PCI capability.

In Example 11, the method of any of Examples 1-10, further comprising: determining a third score from the filtered emergency medical service data set, wherein the third score indicates objective operational performance quality for the filtered emergency medical service data set, wherein the first score and third score are each a different operational score selected from the group consisting of the first, second, third, and fourth operational scores, and merging the first, second, and third scores to form the composite score.

In Example 12, the method of any of Examples 1-11, further comprising: determining a fourth score from the filtered emergency medical service data set, wherein the fourth score indicates objective operational performance quality for the filtered emergency medical service data set, wherein the first, third, and fourth scores are each a different operational score selected from the group consisting of the first, second, third, and fourth operational scores, and merging the first, second, third, and fourth scores to form the composite score.

In Example 13, the method of any of Examples 1-12, further comprising: determining a fifth score from the filtered emergency medical service data set, wherein the fifth score indicates objective operational performance quality for the filtered emergency medical service data set, wherein the first, third, fourth, and fifth scores are each a different operational score selected from the group consisting of the first, second, third, and fourth operational scores, and merging the first, second, third, fourth, and fifth scores to form the composite score.

In Example 14, the method of any of Examples 1-13, further comprising: determining eighth, ninth, and tenth scores from the filtered emergency medical service data set, wherein the eighth, ninth, and tenth scores indicate objective operational performance quality for the filtered emergency medical service data set, wherein the second, eight, ninth, and tenth scores are each a different operational score selected from the group consisting of: a first operational score indicating how rapidly a dispatch center receives an emergency communication and notifies an emergency medical team; a second operational score indicating how rapidly the emergency medical team receives notification from the dispatch center and begins traveling to a location of a medical emergency; a third operational score indicating a duration for which the emergency medical team remains at the location of the medical emergency; and a fourth operational score indicating a proportion of patients who need percutaneous coronary intervention (PCI) and are transported to a medical facility with PCI capability, and merging the first, second, third, fourth, fifth, sixth, seventh, eighth, ninth, and tenth scores to form the composite score.

In Example 15, the method of any of Examples 1-14, wherein the first and second scores are equally weighted when merging the first score and the second score to form the composite score.

In Example 16, the method of any of Examples 1-15, wherein the first and second scores are unequally weighted when merging the first score and the second score to form the composite score.

In Example 17, the method of any of Examples 1-16, wherein the first, second, and composite scores are numerical.

In Example 18, the method of any of Examples 1-17, further comprising sending an alert or notification message to the user based on the composite score.

In Example 19, the method of any of Examples 1-18, further comprising sending an alert or notification message to the user when the composite score falls below a predetermined threshold.

In Example 20, a system for evaluating emergency medical service, according to embodiments of the present invention, includes a processor; a database in communication with the processor; a display device in communication with the processor; wherein the processor is configured to: receive emergency medical service data from the database; filter the emergency medical service data based on a selection criteria to form a filtered emergency medical service data set; determine a first score from the filtered emergency medical service data set, wherein the first score indicates objective clinical performance quality for the filtered emergency medical service data set; determine a second score from the filtered emergency medical service data set, wherein the second score indicates objective operational performance quality for the filtered emergency medical service data set; merge the first score and the second score to form a composite score; and visually display the composite score with the display device.

In Example 21, the system of Example 20, wherein the processor is further configured to display on with the display device a recommendation for improving the composite score.

In Example 22, the system of any of Examples 20-21, wherein the emergency medical service data in the database is at least partly in National EMS Information System (NEMSIS) format.

In Example 23, the system of any of Examples 20-22, wherein the selection criteria is patient age.

In Example 24, the system of any of Examples 20-23, wherein the selection criteria is patients having ST elevated myocardial infarction (STEMI).

In Example 25, the system of any of Examples 20-24, wherein the first score is selected from a group consisting of: a first clinical score indicating how rapidly a twelve lead ECG signal is acquired from a patient after arrival of an emergency medical team at a location of a medical emergency; a second clinical score indicating a proportion of patients whose symptom onset information is documented; a third clinical score indicating a proportion of patients whose vital signs are documented; a fourth clinical score indicating a proportion of patients whose twelve lead ECG signal is documented; a fifth clinical score indicating a proportion of patients who need aspirin and who are actually administered aspirin; and a sixth clinical score indicating a proportion of patients for which a treatment or diagnosis protocol applies and for which such treatment or diagnosis protocol is actually followed.

In Example 26, the system of any of Examples 20-25, wherein the processor is further configured to: determine a third score from the filtered emergency medical service data set, wherein the third score indicates objective clinical performance quality for the filtered emergency medical service data set, wherein the first score and third score are each a different clinical score selected from the group consisting of the first, second, third, fourth, fifth, and sixth clinical scores, and merge the first, second, and third scores to form the composite score.

In Example 27, the system of any of Examples 20-26, wherein the processor is further configured to: determine a fourth score from the filtered emergency medical service data set, wherein the fourth score indicates objective clinical performance quality for the filtered emergency medical service data set, wherein the first, third, and fourth scores are each a different clinical score selected from the group consisting of the first, second, third, fourth, fifth, and sixth clinical scores, and merge the first, second, third, and fourth scores to form the composite score.

In Example 28, the system of any of Examples 20-27, wherein the processor is further configured to: determine a fifth, sixth, and seventh score from the filtered emergency medical service data set, wherein the fifth, sixth, and seventh scores each indicate objective clinical performance quality for the filtered emergency medical service data set, wherein the first, third, fourth, fifth, sixth, and seventh scores are each a different clinical score selected from the group consisting of the first, second, third, fourth, fifth, and sixth clinical scores, and merge the first, second, third, fourth, fifth, sixth, and seventh scores to form the composite score.

In Example 29, the system of any of Examples 20-28, wherein the second score is selected from a group consisting of: a first operational score indicating how rapidly a dispatch center receives an emergency communication and notifies an emergency medical team; a second operational score indicating how rapidly the emergency medical team receives notification from the dispatch center and begins traveling to a location of a medical emergency; a third operational score indicating a duration for which the emergency medical team remains at the location of the medical emergency; and a fourth operational score indicating a proportion of patients who need percutaneous coronary intervention (PCI) and are transported to a medical facility with PCI capability.

In Example 30, the system of any of Examples 20-29, wherein the processor is further configured to: determine a third score from the filtered emergency medical service data set, wherein the third score indicates objective operational performance quality for the filtered emergency medical service data set, wherein the first score and third score are each a different operational score selected from the group consisting of the first, second, third, and fourth operational scores, and merge the first, second, and third scores to form the composite score.

In Example 31, the system of any of Examples 20-30, wherein the processor is further configured to: determine a fourth score from the filtered emergency medical service data set, wherein the fourth score indicates objective operational performance quality for the filtered emergency medical service data set, wherein the first, third, and fourth scores are each a different operational score selected from the group consisting of the first, second, third, and fourth operational scores, and merge the first, second, third, and fourth scores to form the composite score.

In Example 32, the system of any of Examples 20-31, wherein the processor is further configured to: determine a fifth score from the filtered emergency medical service data set, wherein the fifth score indicates objective operational performance quality for the filtered emergency medical service data set, wherein the first, third, fourth, and fifth scores are each a different operational score selected from the group consisting of the first, second, third, and fourth operational scores, and merge the first, second, third, fourth, and fifth scores to form the composite score.

In Example 33, the system of any of Examples 20-32, wherein the processor is further configured to: determine eighth, ninth, and tenth scores from the filtered emergency medical service data set, wherein the eighth, ninth, and tenth scores indicate objective operational performance quality for the filtered emergency medical service data set, wherein the second, eight, ninth, and tenth scores are each a different operational score selected from the group consisting of: a first operational score indicating how rapidly a dispatch center receives an emergency communication and notifies an emergency medical team; a second operational score indicating how rapidly the emergency medical team receives notification from the dispatch center and begins traveling to a location of a medical emergency; a third operational score indicating a duration for which the emergency medical team remains at the location of the medical emergency; and a fourth operational score indicating a proportion of patients who need percutaneous coronary intervention (PCI) and are transported to a medical facility with PCI capability, and merge the first, second, third, fourth, fifth, sixth, seventh, eighth, ninth, and tenth scores to form the composite score.

In Example 34, the system of any of Examples 20-33, wherein the first and second scores are equally weighted when merging the first score and the second score to form the composite score.

In Example 35, the system of any of Examples 20-34, wherein the first and second scores are unequally weighted when merging the first score and the second score to form the composite score.

In Example 36, the system of any of Examples 20-35, wherein the first, second, and composite scores are numerical.

In Example 37, the system of any of Examples 20-36, wherein the processor is further configured to send an alert or notification message to the user based on the composite score.

In Example 38, the system of any of Examples 20-37, wherein the processor is further configured to send an alert or notification message to the user based on the composite score falling below a predetermined threshold.

In Example 39, a method for evaluating emergency medical service, according to embodiments of the present invention, includes receiving first emergency medical service data from a first database, the first emergency medical service data collected from medical events to which a first person or group responded; filtering the first emergency medical service data based on a selection criteria to form a first filtered emergency medical service data set; determining a first score from the first filtered emergency medical service data set, wherein the first score indicates objective clinical performance quality for the first filtered emergency medical service data set; determining a second score from the first filtered emergency medical service data set, wherein the second score indicates objective operational performance quality for the first filtered emergency medical service data set; merging the first score and the second score to form a first composite score; receiving second emergency medical service data from a second database, the second emergency medical service data collected from medical events to which a second person or group responded; filtering the second emergency medical service data based on the selection criteria to form a second filtered emergency medical service data set; determining a third score from the second filtered emergency medical service data set, wherein the third score indicates objective clinical performance quality for the second filtered emergency medical service data set; determining a fourth score from the second filtered emergency medical service data set, wherein the fourth score indicates objective operational performance quality for the second filtered emergency medical service data set; merging the third score and the fourth score to form a second composite score; comparing the first composite score with the second composite score to compare emergency medical service performance of the first person or group with the second person or group, and visually displaying a result of the comparison to a user.

In Example 40, the method of Example 39, wherein the first person or group is a first person, and wherein the second person or group is a second person.

In Example 41, the method of any of Examples 39-40, wherein the first person or group is a first group of individuals within a company, and wherein the second person or group is a second group of individuals within the company.

In Example 42, the method of any of Examples 39-41, wherein the first person or group is a first group of individuals within a first company, and wherein the second person or group is a second group of individuals within a second company other than the first company.

In Example 43, the method of any of Examples 39-42, wherein the first person or group is a first group of individuals at a first geographic location, and wherein the second person or group is a second group of individuals at a second geographic location other than the first geographic location.

In Example 44, the method of any of Examples 39-43, wherein the first person or group is a first ambulance company, and wherein the second person or group is a second ambulance company.

In Example 45, the method of any of Examples 39-44, performed as part of a municipal or governmental contract bidding process for provision of emergency medical services.

In Example 46, the method of any of Examples 39-45, wherein the first and second databases form part of the same database.

In Example 47, the method of any of Examples 39-46, further comprising sending an alert or notification message to the user based on the composite score.

In Example 48, the method of any of Examples 39-47, further comprising sending an alert or notification message to the user when the composite score falls below a predetermined threshold.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 3 illustrates selected database elements that may be used in an emergency service evaluation and scoring system, according to embodiments of the present invention.

FIG. 14 illustrates an example of an ST segment elevation myocardial infarction ("STEMI") score as a combination of ten performance measure scores, according to embodiments of the present invention.

Figure 1:
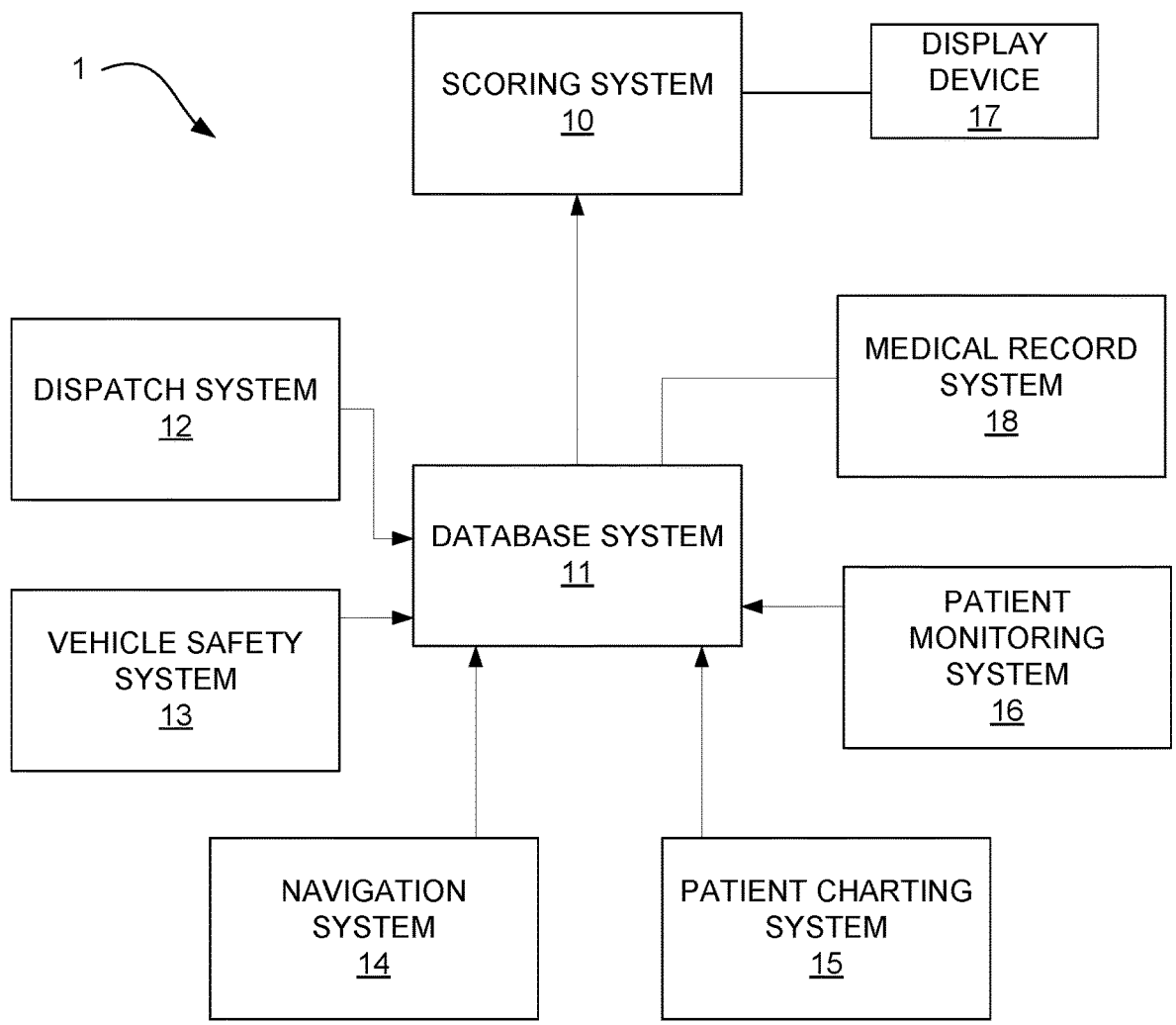
FIG. 1 illustrates a system for emergency service evaluation and scoring, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more comprehensive system 1 for evaluation and scoring of an emergency service is illustrated in FIG. 1. System 1 includes a database system 11, which includes a computer-readable medium or media on which data received from other systems may be stored and retrieved. The database system 11 is communicably coupled with a dispatch system 12, a vehicle safety system 13, a navigation system 14, a patient charting system 15, and a patient monitoring system 16, according to embodiments of the present invention. Database system 11 may also be communicably coupled with other systems involved in emergency medical response, according to embodiments of the present invention.

As used herein, "communicably coupled" is used in its broadest sense to refer to a direct or indirect connection which permits information and/or signals to be transferred, and includes for example wired, wireless, and networked connections. The dispatch system 12 facilitates the receipt of calls or requests for emergency medical service, as well as the sending of dispatch requests or instructions to emergency responders, such as ambulances. The dispatch system 12 may be a computer-aided dispatch ("CAD") system, and may permit tracking of location and/or status of vehicles, according to embodiments of the present invention. The dispatch system 12 may provide data for the database 11, including for example the time at which an emergency medical call (e.g. 911 call) is received, the time when an ambulance is contacted or dispatched, the address of the medical emergency, the address of the facility to which the patient is to be transported, the patient's name and other biographical information, and other information related to dispatch. The dispatch system 12 may be a RescueNet Dispatch system available from ZOLL Medical Corporation, according to embodiments of the present invention.

The vehicle safety system 13 monitors safety and speed parameters of a vehicle, for example an ambulance, involved in emergency medical response. The vehicle safety system 13 may provide data for the database 11, including for example times of, or numbers of, speed or acceleration violations in the operation of the vehicle. The vehicle safety system 13 may be a RescueNet Road Safety system available from ZOLL Medical Corporation, according to embodiments of the present invention. Other examples of vehicle safety systems 13 are described in U.S. Provisional Patent Application Ser. No. 61/656,527, filed on Jun. 7, 2012, the entire content of which is incorporated by reference herein.

The navigation system 14 provides location and routing information to a driver or pilot of an emergency response vehicle or vessel. The navigation system 14 may provide data for the database 11, including for example the beginning address or location, waypoint addresses or locations, the ending address or location, route information, beginning time, waypoint times, and/or ending times. The navigation system 14 may be a RescueNet Navigator system available from ZOLL Medical Corporation, according to embodiments of the present invention.

The patient charting system 15 collects biographical, clinical, and medical information from the patient or patients being treated in the emergency response, according to embodiments of the present invention. Information may be entered manually and/or automatically into the patient charting system, to create documentation regarding the patient encounter. The patient charting system 15 may provide data for the database 11, including for example the patient's name, address, weight, gender, chief complaint, medical history, other biographic data, heart rate, blood pressure, and other vital sign data, electrocardiographs ("ECGs") and other data from clinical instruments, and other data about the patient. The patient charting system 15 may be a RescueNet ePCR system available from ZOLL Medical Corporation, according to embodiments of the present invention.

The patient monitoring system 16 monitors the patient during the emergency medical encounter, collecting clinical and/or physiological data from or about the patient, according to embodiments of the present invention. The patient monitoring system 16 may be, for example, a medical monitor or defibrillator. The patient monitoring system 16 may provide data for the database 11, including for example heart rate, blood pressure, ECGs, blood oxygen saturation, and other vital sign data. The patient monitoring system 16 may be an X Series Monitor Defibrillator available from ZOLL Medical Corporation, according to embodiments of the present invention.

The medical record system 18, which may also be referred to as a healthcare information system 18, stores records about one or more patients, for example information collected from prior patient encounters, public and/or private insurance, billing, and/or membership databases, and/or medical care facilities such as hospitals, clinics, and/or physicians' offices. According to some embodiments of the present invention, the database system 11 and/or scoring system 10 may be configured to pull information from medical record system 18 for use in various scoring activities. In some cases, medical record system 18 may be an external, proprietary, and/or historical database, for example a database accessible through a network, according to embodiments of the present invention. Medical record system 18 may store information such as, without limitation, medical history, billing information, operations and resource management systems, and the like.

Some data generated by systems 12-16, 18 may overlap or be duplicative. In addition, systems 12-16, 18 may retrieve certain portions of data from database system 11, for example to minimize such duplication of data. Also, database system 11 may include a single composite database in which all of the data from systems 12-16, 18 is stored; alternatively, database system 11 may be formed by multiple database systems 11 formed of multiple databases or sub-databases, which may be in the same location, or distributed across multiple locations, and/or part of a networked cloud database structure. According to some embodiments, each system 12-16, 18 includes its own database which forms a part of database system 11, according to embodiments of the present invention. According to some embodiments of the present invention, some or all of the emergency medical information in the database system 11 is stored in National EMS Information System ("NEMSIS") format, which is a dataset standard for the emergency medical service ("EMS") industry. Such information may be stored in NEMSIS Version 2.2.1 format, for example. According to some embodiments of the present invention, system 1 is a system used by an emergency medical response company; multiple companies may have their own systems 1, or systems that include components or subsets of systems 12-16, according to embodiments of the present invention.

Scoring system 10 is communicably coupled to database system 11. Scoring system 10 is configured to pull selected data from database 11, and/or pull all data from database 11, and calculate various objective scores that reflect the quality of performance of the emergency medical services company, team, provider, or group of companies, teams, or providers, in the emergency service chain. This may be done by calculating scores for specific performance factors, and then aggregating such specific scores into a composite score that reflects broader and/or overall performance. Such specific performance factors may be clinical or operational, and may relate to times involved in the emergency response and/or procedures followed in the emergency services, according to embodiments of the present invention.

Scoring system 10 may be communicably coupled to other database systems besides database system 11, and may use objective data from each database in the same calculations to provide performance scores which can be compared as between organizations, individuals, patients, response crews, geographic areas, and times, according to embodiments of the present invention.

Figure 2:
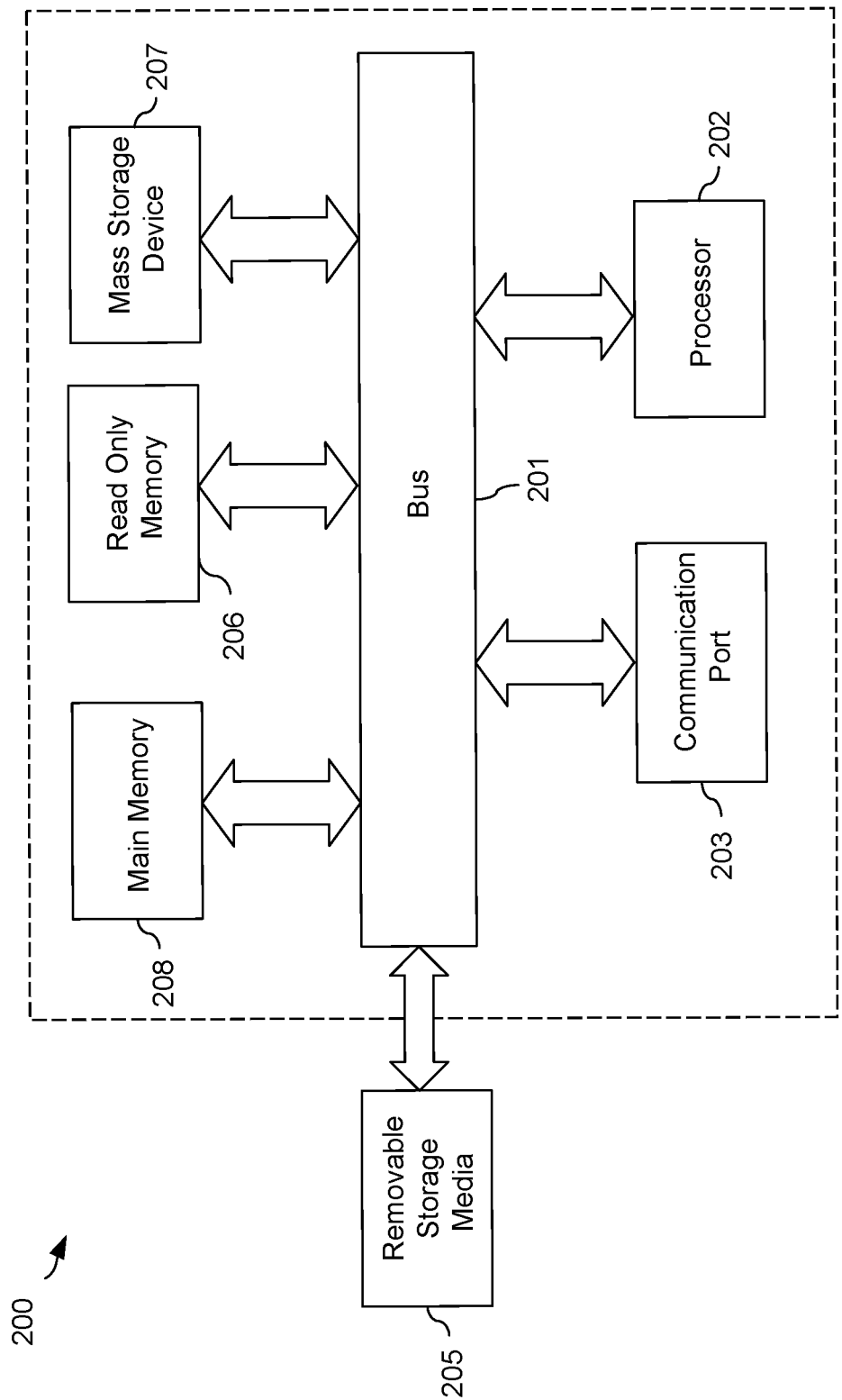
FIG. 2 illustrates a computer system, according to embodiments of the present invention.

FIG. 2 is an example of a computer or computing device system 200 with which embodiments of the present invention may be utilized. For example, systems 11-16 may each be or include a computer system 200, according to embodiments of the present invention. According to the present example, the computer system includes a bus 201, at least one processor 202, at least one communication port 203, a main memory 208, a removable storage media 205, a read only memory 206, and a mass storage 207.

Processor(s) 202 can be any known processor, such as, but not limited to, an Intel® Itanium® or Itanium 2® processor(s), or AMO® Opteron® or Athlon MP® processor(s), or Motorola® lines of processors, or any known microprocessor or processor for a mobile device, such as, but not limited to, ARM, Intel Pentium Mobile, Intel Core i5 Mobile, AMO A6 Series, AMO Phenom II Quad Core Mobile, or like devices. Communication port(s) 203 can be any of an RS-232 port for use with a modem based dialup connection, a copper or fiber 10/100/1000 Ethernet port, or a Bluetooth® or WiFi interface, for example. Communication port(s) 203 may be chosen depending on a network such a Local Area Network (LAN), Wide Area Network (WAN), or any network to which the computer system 200 connects. Main memory 208 can be Random Access Memory (RAM), or any other dynamic storage device(s) commonly known to one of ordinary skill in the art. Read only memory 206 can be any static storage device(s) such as Programmable Read Only Memory (PROM) chips for storing static information such as instructions for processor 202, for example.

Mass storage 207 can be used to store information and instructions. For example, flash memory or other storage media may be used, including removable or dedicated memory in a mobile or portable device, according to embodiments of the present invention. As another example, hard disks such as the Adaptec® family of SCSI drives, an optical disc, an array of disks such as RAID (e.g. the Adaptec family of RAID drives), or any other mass storage devices may be used. Mass storage 207 may also include network accessed storage devices, for example cloud-based storage systems, according to embodiments of the present invention. Bus 201 communicably couples processor(s) 202 with the other memory, storage and communication blocks. Bus 201 can be a PCI/PCI-X or SCSI based system bus depending on the storage devices used, for example. Removable storage media 205 can be any kind of external hard-drives, floppy drives, flash drives, zip drives, compact disc-read only memory (CD-ROM), compact disc-re-writable (CD-RW), or digital video disk-read only memory (DVD-ROM), for example. The components described above are meant to exemplify some types of possibilities. In no way should the aforementioned examples limit the scope of the invention, as they are only exemplary embodiments of computer system 200 and related components.

Scoring system 10 may be configured to calculate a wide range of various performance scores based on a wide range of factors. One example described herein is the calculation of an ST segment elevation myocardial infarction ("STEMI") score, which looks at data from database system 11 across numerous EMS responses and transports for patients with STEMI conditions, and calculates an objective STEMI score which takes into account at least one clinical factor and at least one operational factor. A clinical factor or score is a factor or score that relates to the quality of performance of clinical care given to the patient, for example whether and how rapidly medications were administered, vital signs monitored, ECG signals acquired, and/or treatment and diagnosis protocols followed. Clinical factors include all aspects of healthcare provided, including all structural and resource capabilities associated with such healthcare. An operational factor or score is a factor or score that relates to the quality of performance of business, logistical, or other operations not directly related to patient clinical care, for example relating to responding to emergency calls, and transporting the patient. Operational factors include all operational activities, including business practices such as billing, according to embodiments of the present invention.

FIGS. 4-13 each illustrate the calculation of one of ten subcomponents of the STEMI score. FIG. 14 illustrates an example tally of the ten subcomponents to form a composite STEMI score. FIGS. 3-14 illustrate just one, non-limiting example of how emergency medical service systems may be scored and/or evaluated and/or compared, according to embodiments of the present invention. Based on the disclosure provided herein, one of ordinary skill in the art will appreciate how the systems and methods described herein may be applied to other similar and related data or scenarios, for objective evaluation and/or scoring.

FIG. 3 illustrates examples of data elements that may be stored in database system 11 and used by scoring system 10 for the calculations described in FIGS. 4-13. The data elements beginning with E are NEMSIS Version 2.2.1 data elements, and the last three in the list are non-NEMSIS data elements which may be collected from systems 12-16, 18 and/or stored in database system 11, and are objective data elements which would likely be collected by most emergency medical service systems. While certain NEMSIS data elements are listed which are used for the scoring examples provided herein, one of ordinary skill in the art will appreciate, based on the disclosure provided herein, that various other NEMSIS data elements may be used to calculate other related, similar, or additional EMS scores according to embodiments of the present invention. As such, the NEMSIS NHTSA Version 2.2.1 Data Dictionary and supporting documentation as it exists as of May 10, 2013, available at www.nemsis.org, is hereby incorporated by reference in its entirety.

Figure 4:
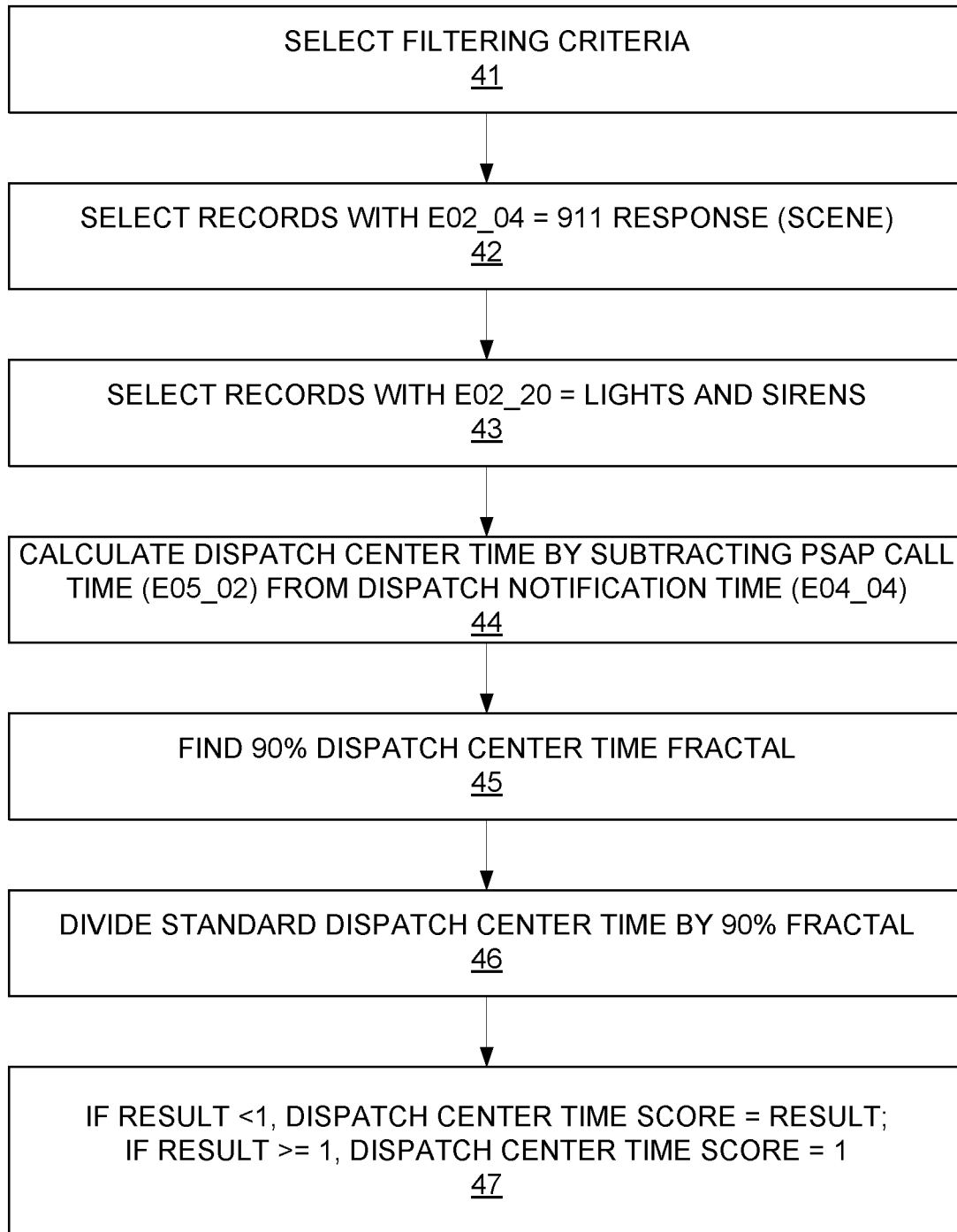
FIG. 4 depicts a flow chart illustrating a method for determining a dispatch center time score, according to embodiments of the present invention.

FIG. 4 depicts a flow chart illustrating a method for determining a dispatch center time score, according to embodiments of the present invention. The dispatch center time is the time beginning with the phone ringing in the emergency (e.g. 911) call center until the EMS unit is notified to respond by dispatch, according to embodiments of the present invention. First, a filtering criteria may be selected (block 41), which specifies to the scoring system 10 which subset of the data in database system 11 is to be used for the scoring analysis. For example, a filtering criteria selection could specify only records for which the NEMSIS data element E02_04 is equal to "911 Response (Scene)," and for which E02_20 is equal to "Lights and Sirens." This would filter out ambulance transport records that involved an interfacility transport or non-emergency transport, for example.

Selection criteria may also be used to identify patient records for EMS acute cardiac patients. For example, the acute cardiac patient records may be identified as any patient whose age is greater than 35 years, where the protocol used E17_01 is equal to "Cardiac Chest Pain," or having any of the following documented for E14_03: "12 Lead ECG-Inferior Ischemia," "12 Lead ECG-Anterior Ischemia," "12 Lead ECG-Lateral Ischemia," or "Left Bundle Branch Block." If a record does not have any of the E17_01 protocols documented, than any records with E19_03 or E09_01 showing a "12 Lead ECG" may be considered an acute cardiac patient. If a record does not have any protocols documented under E17 01, then any records with the following Medication Given (E18_03) or Prior Aid (09_01) documented as "Aspirin" or "Nitroglycerin" may be identified as an acute cardiac patient.

A further subset of the acute cardiac patients include STEM I patients, which includes any patient for which one of the following is documented for data element E14 03: "12 Lead ECG-Inferior Ischemia," "12 Lead ECG-Anterior Ischemia," "12 Lead ECG-Lateral Ischemia," or "Left Bundle Branch Block."

Selection criteria may also involve setting a date range for the records to be scored, patient age, patient gender, patient race, primary impression, and/or other identifiers such as a particular caregiver, a particular patient, a particular crew (e.g. ambulance crew or shift), and/or a particular division. Other criteria may also be employed to filter or select the portions of the data set over which to perform the scoring analysis.

Once the desired records have been selected using any desired filtering criteria, the records with the data element E02_04 equal to "911 Response" (block 42) and with E02_20 equal to "Lights and Sirens" (block 43) may be selected to ensure that only emergency medical service records are being scored. Next, a dispatch center time may be calculated for each record by subtracting the public safety answering point ("PSAP") call time, which is NEMSIS data element E05_02, from the dispatch notification time, which is NEMSIS data element E04_04 (block 44). Next, for all the records being scored, a 90% fractal time may be calculated (block 45), in order to ensure that the extreme data points do not improperly skew the time statistic. A 90% fractal time is the value or measurement at which 90% of all events occur. The 10% of the records with the longest time value are removed from the dataset, and then the maximum value of the remaining dataset is used. Other percentages may be used for the fractal time calculation, according to embodiments of the present invention. Next, in order to calculate the dispatch center time score, a standard dispatch center time is divided by the result of the 90% fractal time calculation (block 46), with the standard dispatch center time being used as a reference point. For example, the national performance measure standard time for dispatch center time is three minutes, so the 90% fractal time may be the denominator under three minutes in order to determine the dispatch center time score. If the result is less than one, the result becomes the dispatch center time score; if the result is greater than one, the dispatch center time score becomes a maximum (e.g. one) (block 47). If less than half of the identified patients have an associated dispatch center time, the score may be set to 0.25 or some other minimum or baseline score, according to embodiments of the present invention.

Figure 5:
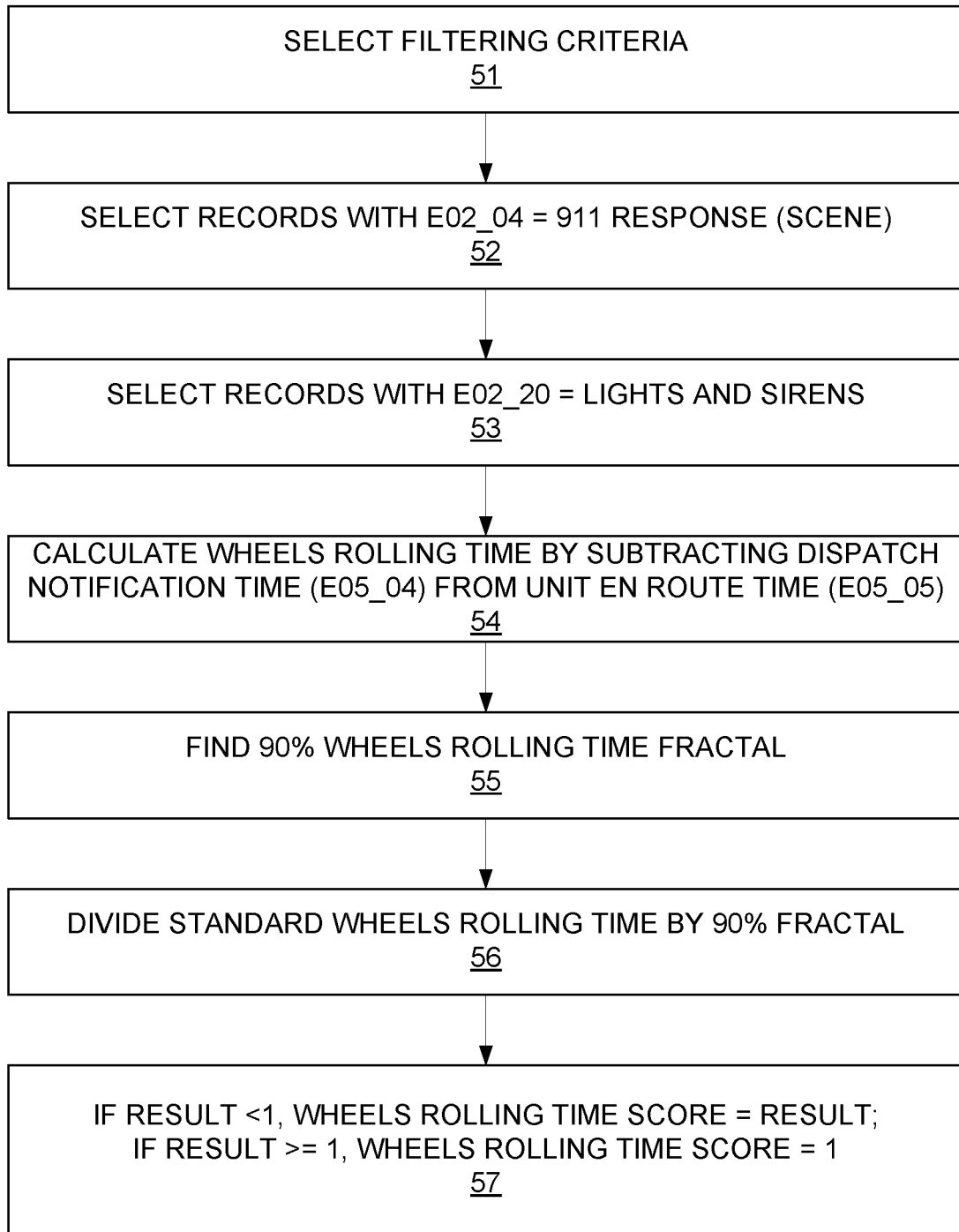
FIG. 5 depicts a flow chart illustrating a method for determining a wheels rolling time score, according to embodiments of the present invention.

FIG. 5 depicts a flow chart illustrating a method for determining a wheels rolling time score, according to embodiments of the present invention. The wheels rolling time is the time beginning with the EMS unit being notified to respond by dispatch and the actual wheels moving (unit en route time) when the EMS vehicle begins moving toward the scene of the emergency, according to embodiments of the present invention. First, a filtering criteria may be selected (block 51), which specifies to the scoring system 10 which subset of the data in database system 11 is to be used for the scoring analysis.

Once the desired records have been selected using any desired filtering criteria, the records with the data element E02_04 equal to "911 Response" (block 52) and with E02_20 equal to "Lights and Sirens" (block 53) may be selected to ensure that only emergency medical service records are being scored. Next, a wheels rolling time may be calculated for each record by subtracting the dispatch notification time, which is NEMSIS data element E05_04, from the unit en route time, which is NEMSIS data element E05_05 (block 54). Next, for all the records being scored, a 90% fractal time may be calculated (block 55), in order to ensure that the extreme data points do not improperly skew the time statistic. Next, in order to calculate the wheels rolling score, a standard wheels rolling time is divided by the result of the 90% fractal time calculation (block 56), with the standard wheels rolling time being a time that is used as a reference point. For example, the national performance measure standard time for wheels rolling time is three minutes, so the 90% fractal time may be the denominator under three minutes in order to determine the wheels rolling time score. If the result is less than one, the result becomes the wheels rolling time score; if the result is greater than one, the wheels rolling time score becomes a maximum (e.g. one) (block 57). If less than half of the identified patients have an associated wheels rolling time, the score may be set to 0.25 or some other minimum or baseline score, according to embodiments of the present invention.

Figure 6:
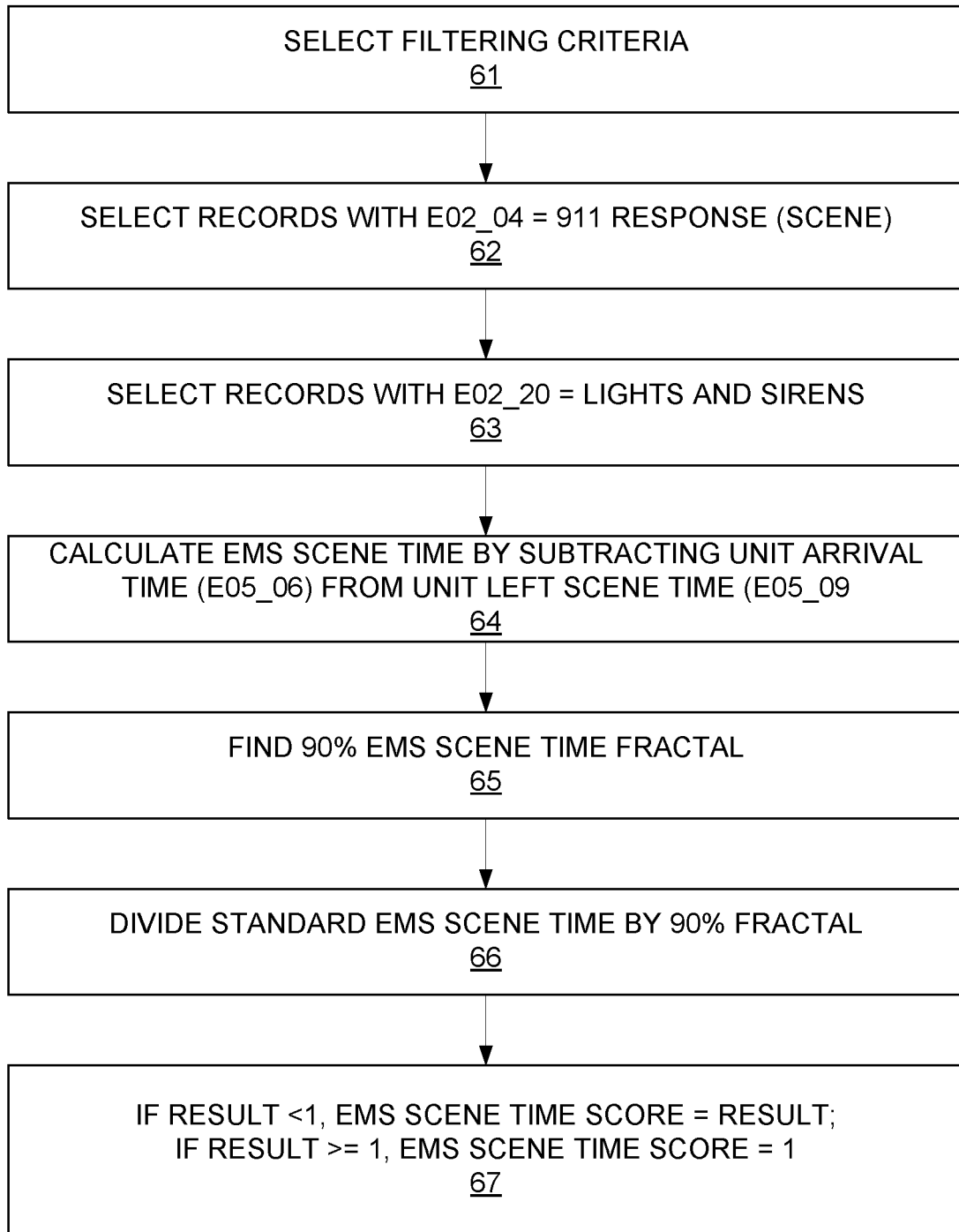
FIG. 6 depicts a flow chart illustrating a method for determining an EMS scene time score, according to embodiments of the present invention.

FIG. 6 depicts a flow chart illustrating a method for determining an EMS scene time score, according to embodiments of the present invention. The EMS scene time is the time beginning when the EMS unit begins moving toward the scene of the emergency and ending when the EMS unit arrives at the scene, according to embodiments of the present invention. First, a filtering criteria may be selected (block 61), which specifies to the scoring system 10 which subset of the data in database system 11 is to be used for the scoring analysis.

Once the desired records have been selected using any desired filtering criteria, the records with the data element E02_04 equal to "911 Response" (block 62) and with E02_20 equal to "Lights and Sirens" (block 63) may be selected to ensure that only emergency response records are being scored. Next, an EMS scene time may be calculated for each record by subtracting the unit en route time, which is NEMSIS data element E05_05, from the unit left scene time, which is NEMSIS data element-E05_09) E05_09 (block 64). Next, for all the records being scored, a 90% fractal time may be calculated (block 65), in order to ensure that the extreme data points do not improperly skew the time statistic. Next, in order to calculate the EMS scene time score, a standard EMS time score may be divided by the result of the 90% fractal time calculation (block 66), with the standard EMS time score being a time that is used as a reference point. For example, the national performance measure standard time for EMS scene time is fifteen minutes, so the 90% fractal time may be the denominator under fifteen minutes in order to determine the EMS scene time score. If the result is less than one, the result becomes the EMS scene time score; if the result is greater than one, the EMS scene time score becomes a maximum (e.g. one) (block 67). If less than half of the identified patients have an associated EMS scene time, the score may be set to 0.25 or some other minimum or baseline score, according to embodiments of the present invention.

Figure 7:
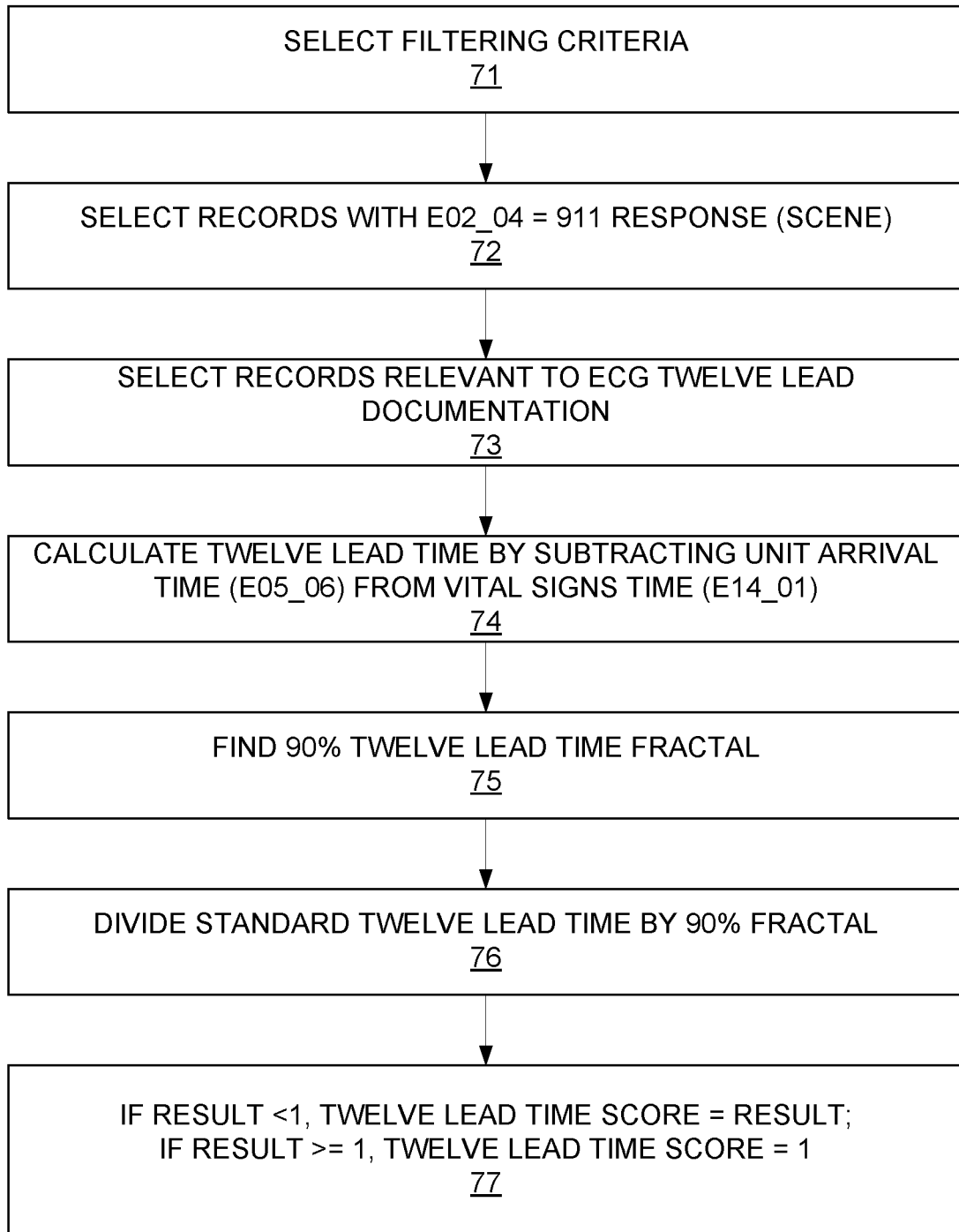
FIG. 7 depicts a flow chart illustrating a method for determining a twelve lead time score, according to embodiments of the present invention.

FIG. 7 depicts a flow chart illustrating a method for determining a twelve lead time score, according to embodiments of the present invention. The twelve lead time is the time beginning with the EMS unit arriving at the scene, and ending when a twelve lead ECG rhythm is documented by the EMS professionals, according to embodiments of the present invention. First, a filtering criteria may be selected (block 71), which specifies to the scoring system 10 which subset of the data in database system 11 is to be used for the scoring analysis.

Once the desired records have been selected using any desired filtering criteria, the records with the data element E02_04 equal to "911 Response" (block 72) and with E02_20 equal to "Lights and Sirens" (block 73) may be selected to ensure that only emergency response records are being scored. Next, an EMS scene time may be calculated for each record by subtracting the unit arrival time, which is NEMSIS data unit E05_06, from the vital signs acquisition time, which is NEMSIS data unit E14_01 (block 74). Next, for all the records being scored, a 90% fractal time may be calculated (block 75), in order to ensure that the extreme data points do not improperly skew the time statistic. Next, in order to calculate the twelve lead time score, a standard twelve lead time is divided by the result of the 90% fractal time calculation (block 76), which is a time that is used as a reference point. For example, the national performance measure standard time for twelve lead acquisition time is ten minutes, so the 90% fractal time may be the denominator under ten minutes in order to determine the twelve lead time score. If the result is less than one, the result becomes the twelve lead time score; if the result is greater than one, the twelve lead time score becomes a maximum (e.g. one) (block 77). If less than half of the identified patients have an associated twelve lead time, the score may be set to 0.25 or some other minimum or baseline score, according to embodiments of the present invention.

Figure 8:
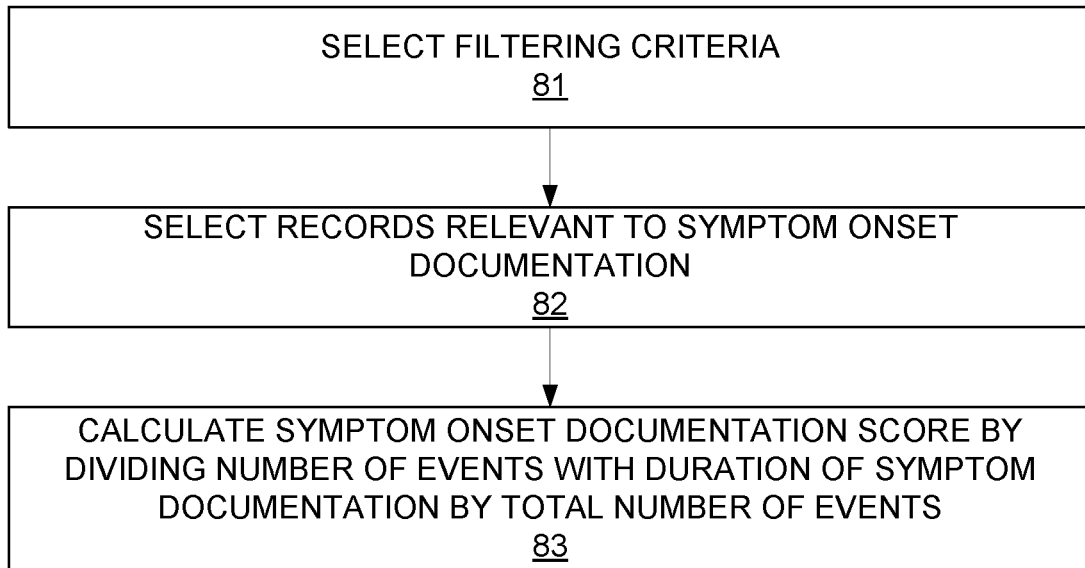
FIG. 8 depicts a flow chart illustrating a method for determining a symptom onset documentation score, according to embodiments of the present invention.

FIG. 8 depicts a flow chart illustrating a method for determining a symptom onset documentation score, according to embodiments of the present invention. First, a filtering criteria may be selected (block 81), which specifies to the scoring system 10 which subset of the data in database system 11 is to be used for the scoring analysis. The records relevant to symptom onset documentation may be selected (block 82) (e.g. the records for which documentation of symptom onset would normally be expected). The symptom onset documentation score may be calculated by dividing the number of events with duration of symptom documentation by the total number of events for which such documentation would normally have been expected (block 83), according to embodiments of the present invention. The national performance measure standard is that all patients (e.g. 100%) should have such symptom onset documentation created, so the score for this category would be a number less than or equal to one, with the score maximum being one.

Figure 9:
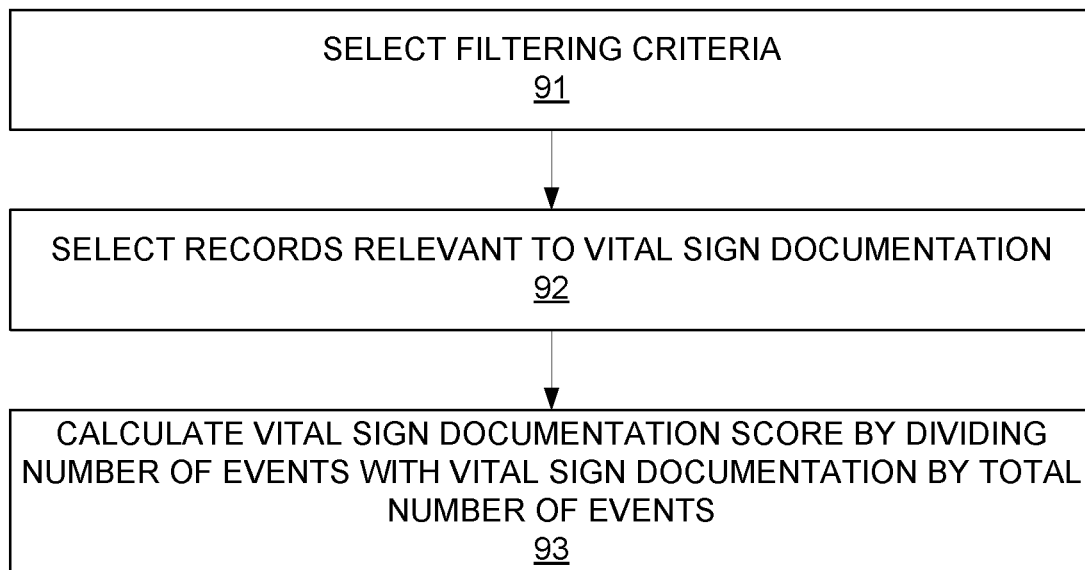
FIG. 9 depicts a flow chart illustrating a method for determining a vital sign documentation score, according to embodiments of the present invention.

FIG. 9 depicts a flow chart illustrating a method for determining a vital sign documentation score, according to embodiments of the present invention. First, a filtering criteria may be selected (block 91), which specifies to the scoring system 10 which subset of the data in database system 11 is to be used for the scoring analysis. The records relevant to vital sign documentation may be selected (block 92) (e.g. the records for which documentation of vital signs would normally be expected). The vital sign documentation score may be calculated by dividing the number of events with vital sign documentation by the total number of events for which such documentation would normally have been expected (block 93), according to embodiments of the present invention. The national performance measure standard is that all patients (e.g. 100%) should have such vital sign documentation created, so the score for this category would be a number less than or equal to one, with the score maximum being one.

Figure 10:
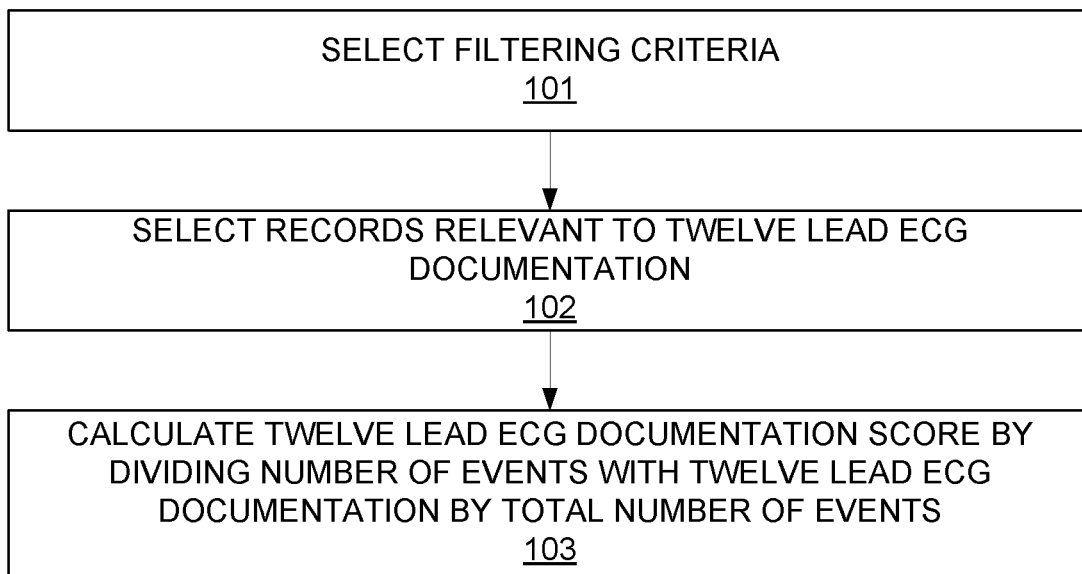
FIG. 10 depicts a flow chart illustrating a method for determining a twelve lead ECG documentation score, according to embodiments of the present invention.

FIG. 10 depicts a flow chart illustrating a method for determining a twelve lead ECG documentation score, according to embodiments of the present invention. First, a filtering criteria may be selected (block 91), which specifies to the scoring system 10 which subset of the data in database system 11 is to be used for the scoring analysis. The records relevant to 12 lead ECG documentation may be selected (block 92) (e.g. the records for which documentation of vital signs would normally be expected). The 12 lead ECG documentation score may be calculated by dividing the number of events with 12 lead ECG documentation by the total number of events for which such documentation would normally have been expected (block 93), according to embodiments of the present invention. The national performance measure standard is that all patients (e.g. 100%) should have such 12 lead ECG documentation created, so the score for this category would be a number less than or equal to one, with the score maximum being one.

Figure 11:
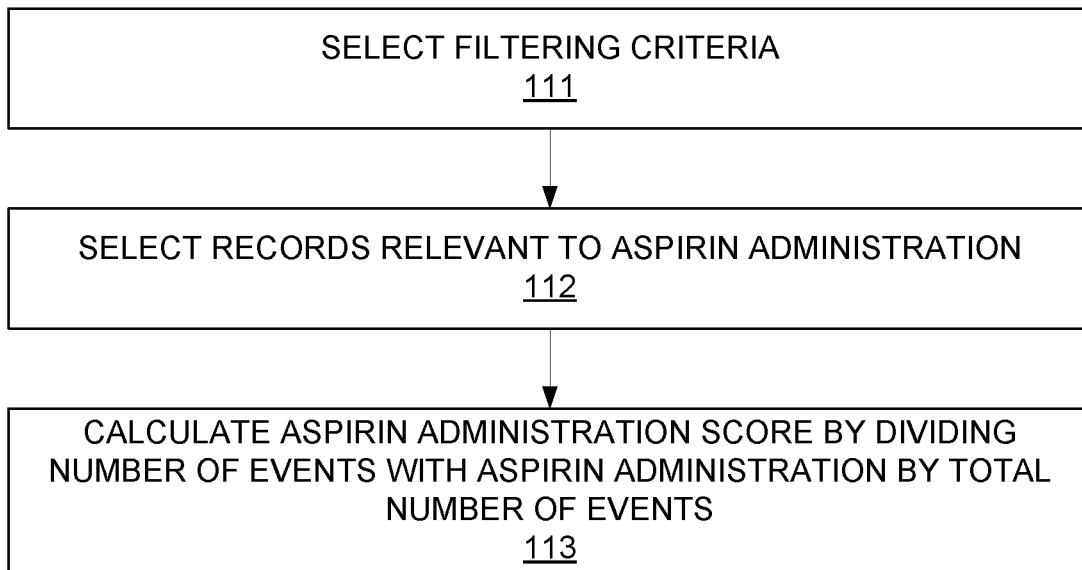
FIG. 11 depicts a flow chart illustrating a method for determining an aspirin administration score, according to embodiments of the present invention.

FIG. 11 depicts a flow chart illustrating a method for determining an aspirin administration score, according to embodiments of the present invention. First, a filtering criteria may be selected (block 111), which specifies to the scoring system 10 which subset of the data in database system 11 is to be used for the scoring analysis. The records relevant to aspirin documentation may be selected (block 112) (e.g. the records for which documentation of aspirin administration would normally be expected). The aspirin administration documentation score may be calculated by dividing the number of events with aspirin administration documentation by the total number of events for which such documentation would normally have been expected (block 113), according to embodiments of the present invention. The national performance measure standard is that all patients (e.g. 100%) should have such aspirin administration documentation created, so the score for this category would be a number less than or equal to one, with the score maximum being one.

Figure 12:
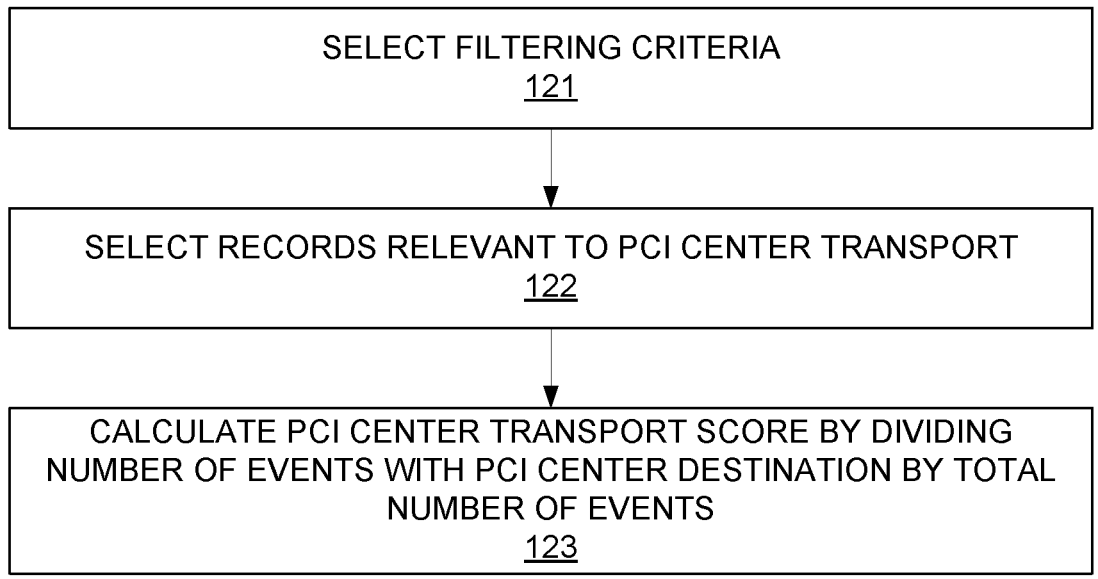
FIG. 12 depicts a flow chart illustrating a method for determining a PCI center transport score, according to embodiments of the present invention.

FIG. 12 depicts a flow chart illustrating a method for determining a PCI center transport score, according to embodiments of the present invention. First, a filtering criteria may be selected (block 121), which specifies to the scoring system 10 which subset of the data in database system 11 is to be used for the scoring analysis. The records relevant to percutaneous cardiac intervention ("PCI") center transport may be selected (block 122) (e.g. the records for which documentation of PCI center transport would normally be expected). For example, if the patient was experiencing an acute cardiac event, it is often preferred to transport the patient to a PCI center rather than a non-PCI general practice hospital. The PCI center transport score may be calculated by dividing the number of events with PCI center transport by the total number of events for which such PCI transport would normally have been expected (block 123), according to embodiments of the present invention. The national performance measure standard is that all patients (e.g. 100%) which would benefit from such PCI center transport are transported to a PCI center, so the score for this category would be a number less than or equal to one, with the score maximum being one. This performance factor benefits from documentation about which hospitals are PCI centers, which is a non-NEMSIS data element, but which may otherwise be tracked.

Figure 13:
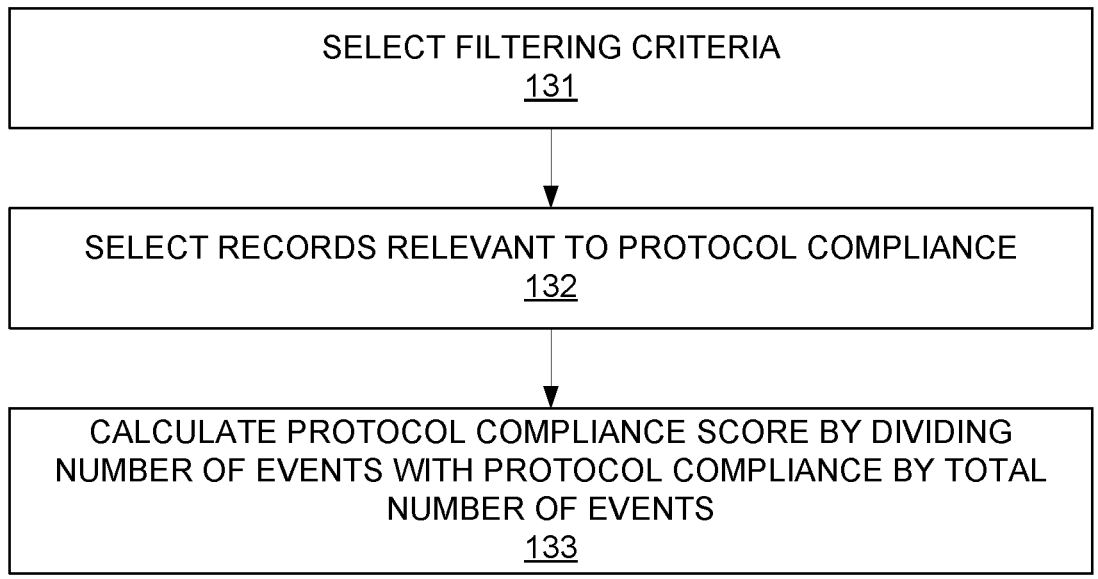
FIG. 13 depicts a flow chart illustrating a method for determining a protocol compliance score, according to embodiments of the present invention.

FIG. 13 depicts a flow chart illustrating a method for determining a protocol compliance score, according to embodiments of the present invention. First, a filtering criteria may be selected (block 131), which specifies to the scoring system 10 which subset of the data in database system 11 is to be used for the scoring analysis. The records relevant to protocol compliance may be selected (block 132) (e.g. the records for which documentation of protocol compliance would normally be expected). The protocol compliance score may be calculated by dividing the number of events with protocol compliance by the total number of events for which such protocol compliance would normally have been expected (block 133), according to embodiments of the present invention. The national performance measure standard is that all patients (e.g. 100%) which would benefit from such protocol compliance are treated according to the protocol, so the score for this category would be a number less than or equal to one, with the score maximum being one.

FIGS. 4-13 illustrate the calculation of a STEMI score, which uses objective (e.g. NEMSIS) data to indicate the effectiveness and/or quality of the emergency medical response. Each of the ten scores calculated in FIGS. 4-13 may be added together to form a composite score, as illustrated in FIG. 14. This objectively calculated score may be used to compare one EMS response system or company to another EMS response system or company. The composite score may be at least one clinical score (as shown in FIG.

14) aggregated with at least one operational score (as shown in FIG. 14), and may include an aggregation or composite of ten or more scores, as described with respect to FIGS. 4-13.

According to embodiments of the present invention, the scoring system 10 may not only generate a score based on emergency medical response criteria, but may also provide performance improvement and/or review enhancement information. For example, if a portion of the STEMI score, or all of the STEMI score, is lower than the industry average, the scoring system 10 may provide recommendations for improving the STEMI score or other score, for example based on statistical data.

While FIGS. 4-14 illustrate the calculation of a STEMI score based on at least one clinical score and at least one operational score (see FIG. 14), similar processes may be used to arrive at other types of scores. Such other types of scores may also include a clinical score and an operational score, for example. The STEMI score may be aggregated with other scores in order to arrive at an overall "EMS Score," to permit the evaluation and comparison of entire EMS platforms, for example. Other scores that may be objectively calculated include, without limitation: EMS Safety, EMS Service Delivery, EMS Response Time, EMS Airway Management, EMS Trauma Care, EMS Stroke Care, EMS Pediatric Care, EMS Cardiac Arrest Care, and/or EMS Customer Satisfaction. If ten scores are calculated, each of which is further calculated from ten sub-scores (similar to the example described with respect to FIGS. 4-14), then an overall EMS Score may be displayed as a score out of one hundred possible points, according to embodiments of the present invention. Other topics or factors which may be scored as described herein include, without limitation, stroke, trauma, airway, cardiac arrest, general medical, general pediatric, shock, billing, safety, and other emergency medical service activities or systems.

While FIG. 14 illustrates simple addition of each of the performance measure scores, in some embodiments the performance measures are regression weighted in order to emphasize or de-emphasize certain performance measures. If some of the performance measure data is not available for a particular platform, then the scoring system 10 may fill in such data based on known statistical methods using average or other data from database system 11, using for example imputation, rescaling, extrapolation, interpolation, normalization, or other methods.

The system 1 may be used as part of a consulting system, whereby businesses seek analysis with system 1 in order to improve performance. System 10 may be configured to provide recommendations, for example automated recommendations, based on observed data from database system 11. For example, system 10 may recognize a correlation between vehicle maintenance frequency and ambulance response times, and suggest vehicle maintenance in response to a low or lower-than-desired EMS Score.

The evaluation and scoring systems and methods described herein may be used internally within an EMS organization, as well as externally across different organizations. Internal use may include the observation of trending, as well as the learning from historical data, involving observing the impact on one parameter when another parameter or variable is changed, according to embodiments of the present invention. Embodiments of the invention may be used for employee benchmarking, as well as benchmarking across various geographic units, or business units, for example. The EMS score may be used across multiple organizations, for example by consumers or hospitals, in order to compare and evaluate the EMS organization.

Embodiments of the present invention may also be used for reimbursement agencies (e.g. insurance agencies) or governmental agencies (e.g. Medicare/Medicaid), for example to verify the performance of a participating EMS organization by requiring a certain minimum aggregate score, or sub-score, in order to reimburse or approve expenses. Embodiments of the present invention may also be used in a request for proposal, or bidding process, for example for a community to ensure that a given EMS organization's performance meets certain expectations before contracting with the EMS organization. The EMS score(s) may further be used in order to determine an audit risk score, such as a Medicare audit risk score, according to embodiments of the present invention.

According to some embodiments of the present invention, scores, such as an EMS Score or a STEMI score, are calculated using at least 50%, or at least 60%, or at least 70%, or at least 80%, or at least 90% of the overall data as standardized data, such as NEMSIS data elements. This maintains objectivity, and also permits practical, objective comparisons to be made across agencies (e.g. a STEMI score of 6.6 will roughly carry the same significance for Agency A as it does for unrelated Agency B).

The scores and/or evaluative information may be obtained in varying increments. For example, for a given EMS system, such as a city or county EMS system, scores may be generated at the agency level, with subset scores at the station or even the EMS response vehicle level. Scores may be created at the crew level, the individual (e.g. paramedic) level, as well as the individual patient level (e.g. individual patient, group of patient types, every patient in the agency).

Embodiments of the present invention involve aggregation of data from multiple products or systems, as illustrated in FIG. 1. Database system 11 may be further configured to store patient survival data, and/or to correlate it with the patient's other records or fields. The scoring system 10 may be configured to recognize patterns and associations between variables, and may further be configured to provide recommendations about how to improve scores or performance based on the historical data. Logical regression analysis may be used to determine which of the performance metrics actually impact patient survival, or some other patient benefit, according to embodiments of the present invention. The scoring system 10 may also be configured to rebalance and/or re-weight the sub scores based on such historical data and analysis, according to embodiments of the present invention.

The scoring system 10 may be configured to provide an alarm or other message to a user based on such recommendations and/or correlations and/or predictions. For example, if the scoring system 10 notices that female acute cardiac patients over the age of 30 respond much more favorably to aspirin administration within two minutes and fifteen seconds, rather than the industry target of three minutes, the scoring system 10 may alert the user, for example via a message or sound on display device 17, that aspirin should be administered sooner when a female acute cardiac patient over age 30 is recognized by the scoring system 10. As such, the scoring system 10 may play a part in a clinical decision support process, according to embodiments of the present invention.

According to embodiments of the present invention, scoring system 10 uses nonlinear scoring systems, for example weighted scoring systems. Such weighting may further be configured to change or be customized, for example automatically, over time and as additional data sets are gathered. For instance, the effects of each parameter on an actual outcome of the patient may be measured, and the relative effects of such parameters may be placed into score weights that become part of scoring system 10, according to embodiments of the present invention. As one non-limiting example, the "door-to-balloon time" or the time it takes the patient to be transported from the location of the patient's heart attack to the time at which a catheter intervention is performed (e.g. a balloon catheter intervention), is known to affect patient survival rates. Each of the components, both clinical and operational, that form part of the door-to-balloon time are known, for example are known using NEMSIS dataset elements. The relative weights of the door-to-balloon time elements may simply be percentages of the total door-to-balloon time, and/or may be measured and estimated from data generated from prior studies, retrospective data from an EMS system, and/or prospectively collected data, of which a statistical analysis provides a logistic regression which may be used to generate a formula correlating the relative linear effects of each of the component variables, according to embodiments of the present invention. A nonlinear regression may also be employed, which may for example involve polynomial or exponential terms. The weighting of the different components in the score permits a system to actually focus on changing the elements (e.g. inputs or variables) of the system that will most affect the desired outcomes (e.g. patient survival), so as to promote cost efficiency and other outcomes, according to embodiments of the present invention.

Statistical process control tools may be used to track performance levels of each of the score components, or system components, along with an overall or composite score, according to embodiments of the present invention. Such tools may include, but are not limited to, standard statistical methods such as analysis of variance, chi-squared analysis, control charts, analysis of correlation, linear modeling, histograms, pareto analysis, regression analysis, root cause analysis, scatter analysis, and stratification.

As described above, the data set for which scoring is performed by scoring system 10 may be filtered and/or grouped so as to determine a score for a particular aspect of a larger EMS process. For example, the data elements that have an impact on door-to-balloon score may be isolated, as well as elements relating to dispatch time. Such aggregated, group scores provide information about functional performance that may not be possible with an aggregated, overall score for an entire emergency medical service system, for example. Such data elements may further be grouped and/or subdivided into different time spans and/or different personnel or geographic areas, to evaluate and/or compare such groups or subdivisions with respect to each other, with respect to other organizations, and/or with respect to past performance, according to embodiments of the present invention. Such customized scoring may also facilitate the pinpointing of weaker aspects of the emergency medical services system, thereby making it easier to improve the system and thus improve the score. In other words, customized or group scoring permits scoring system 10 to identify the portions of the emergency medical services system that are weak and need additional process improvements and/or resources.

Figure 15:
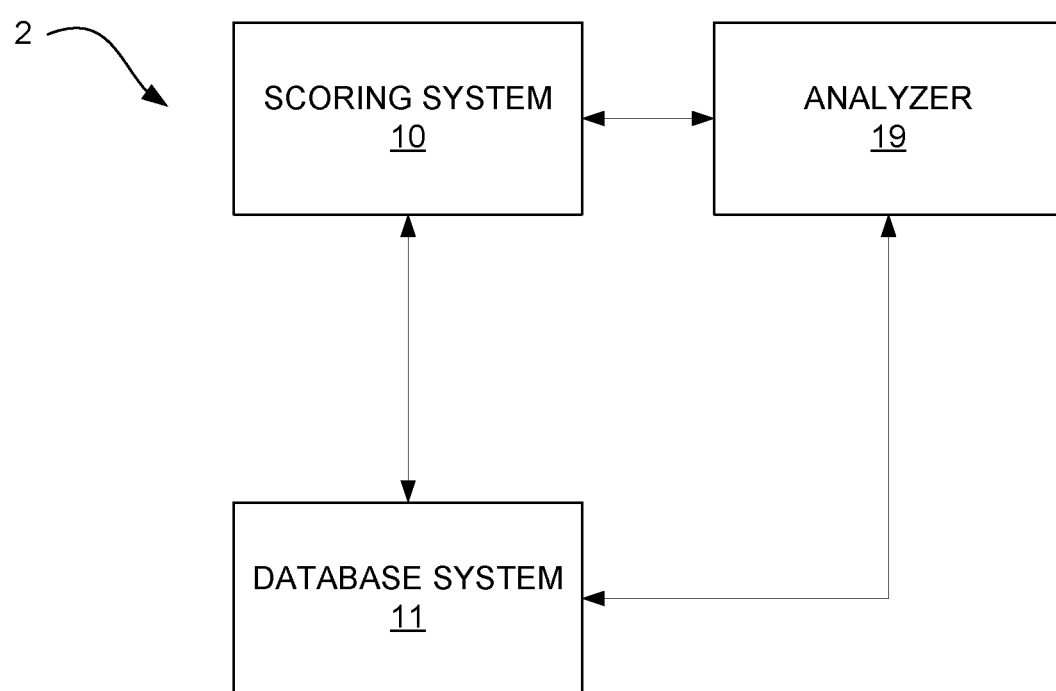
FIG. 15 illustrates a system for analysis of scores, according to embodiments of the present invention.
Figure 16:
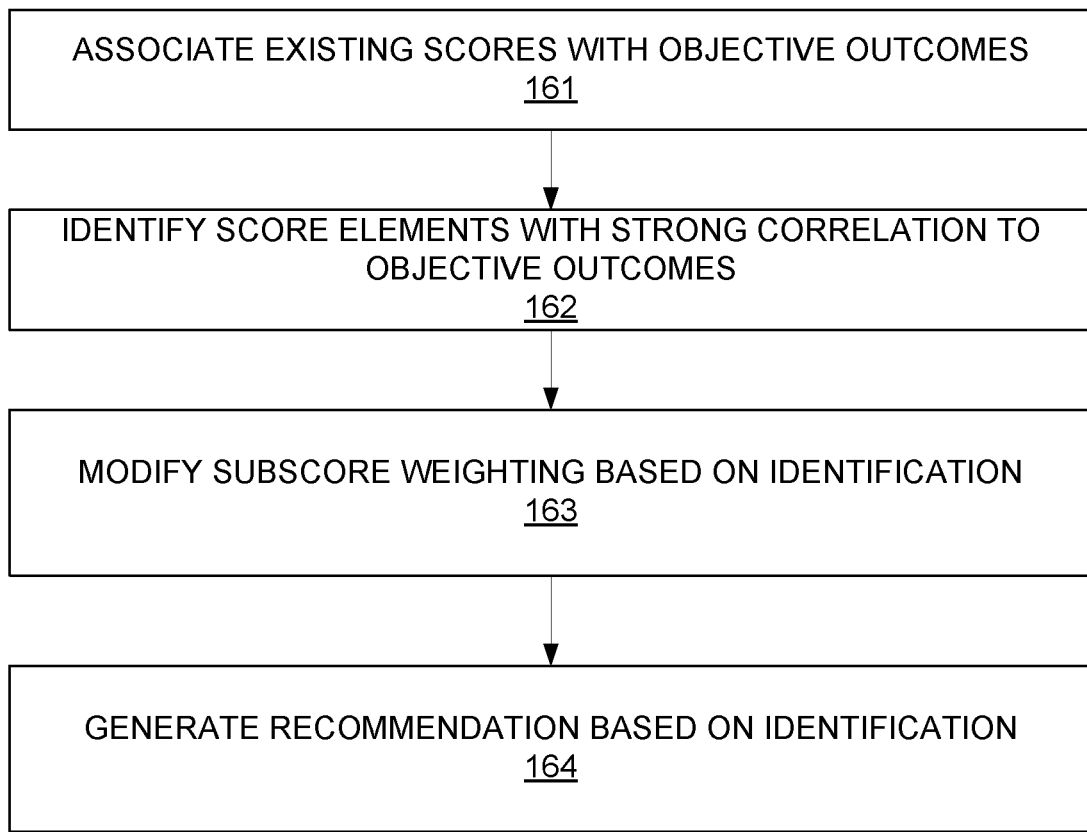
FIG. 16 depicts a flow chart illustrating a method for identifying correlations between scoring elements and desired outcomes, according to embodiments of the present invention.

FIG. 15 illustrates a system 2 for analysis of scores, according to embodiments of the present invention. FIG. 16 depicts a flow chart illustrating a method for identifying correlations between scoring elements and desired outcomes, according to embodiments of the present invention. An analyzer 19 may be communicably coupled with scoring system 10 and/or database system 11, according to embodiments of the present invention. The analyzer 19 may obtain information about objective outcomes for emergency medical events, from database 11 and/or from another database (e.g. medical record system 18) and associate such outcomes with existing scores (block 161). Such outcomes may be, for example, patient survival statistics, and/or patient recovery statistics, and/or patient survival time statistics, and/or patient outcome statistics, according to embodiments of the present invention. In this manner, the analyzer 19 (which may be a computer system 200 and/or a business implemented process) may be configured to use statistical analysis to determine correlations between objective outcomes and scores or subscores or elements of scores (block 162), according to embodiments of the present invention. Such correlations may be used to modify the weighting of a regression-weighted or nonlinearly-weighted scoring algorithm (block 163), for example by giving the most weight to the scoring element that correlates most closely with patient survival for the particular condition which the patient exhibited.

The analyzer 19 may also generate one or more recommendations based on the identification of the correlation (block 164), for example the analyzer 19 may generate a message indicating that the patient survival rate may be improved by shortening the time before a STEM I patient receives aspirin treatment, according to embodiments of the present invention. The analyzer 19 specifies one or more operational and/or clinical performance elements that may need improvement in order to boost aggregate score and/or subscore, according to embodiments of the present invention. These correlations may be performed using well-known statistical analysis methods, for example statistical process control, six-sigma, or others, according to embodiments of the present invention. According to some embodiments of the present invention, the scoring system 10 and/or the analyzer 19 are proprietary, and a consultant or other person uses the scoring system 10 and/or analyzer 19 to audit, or provide consulting services, to an emergency medical services organization in order to provide one or more reports to the emergency medical services organization telling the organization how to improve its emergency medical services based on scoring and analysis as described herein, and related processes. According to some embodiments of the present invention, the scoring system 10 and/or the analyzer 19 are proprietary, and a consultant or other person uses the scoring system 10 and/or analyzer 19 to help municipalities and/or hospitals decide which emergency medical service organization to use for a particular project.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system configured to process emergency medical service (EMS) data for clinical decision support, the system comprising:
 a database system configured to
  communicably couple to a medical record system and an EMS evaluation system,
  communicably couple to a computer aided dispatch system that is associated with a dispatch center remotely located from an EMS transport vehicle and that is configured to track a location and status of the EMS transport vehicle, communicably couple with a navigation system that is configured to determine routing information for the EMS transport vehicle, receive, from the computer aided dispatch system, dispatch data comprising biographical data of a patient and at least one time associated with providing emergency medical services to the patient, the emergency medical services corresponding to the EMS transport vehicle, receive, from the navigation system, the routing information for the EMS transport vehicle, pull, from the medical record system, medical data comprising outcome data for emergency medical events, compile the dispatch data, the routing information, and the medical data into a data set, filter the data set based on at least one selection criteria, thereby generating a filtered data set, and provide, to the EMS evaluation system, the filtered data set, the filtered data set comprising at least a portion of the dispatch data and at least a portion of the medical data; and the EMS evaluation system, wherein the EMS evaluation system is configured to determine an EMS performance score based at least in part on the dispatch data, apply statistical modeling to the EMS performance score and the outcome data for emergency medical events, determine one or more correlations between the EMS performance score and the outcome data based on the statistical modeling, generate a performance recommendation based on the one or more correlations, and provide the clinical decision support by providing the performance recommendation for a user at a display device.

2. The system of claim 1, wherein the dispatch data comprises one or more of a time at which an emergency medical call is received, a time at which an ambulance is dispatched, an address of a medical emergency, or an address of a facility to which the patient is to be transported.

3. The system of claim 1, wherein the patient is a patient for whom an emergency response has been requested, and wherein the data set comprises times involved in the emergency response and procedures followed in the emergency response.

4. The system of claim 3, wherein the times involved in the emergency response comprise one or more of a door-to-balloon time or a scene time.

5. The system of claim 1, wherein the outcome data comprises one or more of retrospective data or prospectively collected data.

6. The system of claim 1, wherein the EMS evaluation system is configured to determine a correlation between an element of the EMS performance score and the outcome data based on the statistical modeling.

7. The system of claim 1, wherein the outcome data comprises one or more of patient survival statistics, patient recovery statistics, patient survival times, or patient outcome statistics.

8. The system of claim 1, wherein the database system is configured to determine whether the performance recommendation is likely to impact patient survival or other patient benefit based on the statistical modeling.

9. The system of claim 5, wherein the EMS evaluation system is configured to provide a user notification that the performance recommendation deviates from an industry standard based on the statistical modeling and at least one of the biographical data of the patient or the medical data.

10. The system of claim 1, wherein the at least one selection criteria filters the data set according to emergency and non-emergency transport records.

11. The system of claim 1, wherein the at least one selection criteria filters the data set based on acute cardiac records.

12. The system of claim 1, wherein the at least one selection criteria filters the data set based on one or more of a date range, a primary impression, or a geographic area.

13. The system of claim 1, wherein the performance recommendation specifies a clinical performance element.

14. The system of claim 13, wherein the performance recommendation comprises an alert specifying a timing of a drug administration to the patient.

15. The system of claim 1, wherein:
the routing information includes one or more of vehicle location data, vehicle routing data, beginning time, waypoint time, or ending times, and
the filtered data set provided to the EMS evaluation system includes at least a portion of the routing information.

16. The system of claim 1, wherein the database system is further configured to:
receive, from a patient monitoring system, monitoring data comprising one or more of clinical data of the patient or physiological data of the patient,
wherein the filtered data set provided to the EMS evaluation system comprises the monitoring data.

17. The system of claim 1, wherein the database system is further configured to:
receive, from a charting system, charting data comprising one or more of the biographical data of the patient, clinical data of the patient, or the medical data,
wherein the filtered data set provided to the EMS evaluation system comprises the charting data.

18. The system of claim 17, wherein the charting data comprises one or more of documentation of symptom onset information, documentation of patient vital signs, documentation of twelve-lead ECG, or documentation of drug administration.

19. The system of claim 1, wherein the performance recommendation specifies a composite performance element merged from an operational performance element and a clinical performance element.

20. The system of claim 1, wherein the data set comprises data elements associated with geographic areas.

21. The system of claim 1, wherein the medical record system comprises information collected from a billing database.

22. The system of claim 1, wherein the EMS evaluation system is configured to provide the clinical decision support for the user via a message or a sound at the display device.

* * * * *